US009060791B2

(12) United States Patent
Slatkine

(10) Patent No.: US 9,060,791 B2
(45) Date of Patent: Jun. 23, 2015

(54) DEVICE FOR INTERMITTENTLY PERFORMING CARE SESSIONS TO FORM A LARGE SKIN AREA CARE

(76) Inventor: Michael Slatkine, Herzlia (IL)

( * ) Notice: Subject to any disclaimer, the term of this patent is extended or adjusted under 35 U.S.C. 154(b) by 22 days.

(21) Appl. No.: 13/499,934

(22) PCT Filed: Oct. 3, 2010

(86) PCT No.: PCT/IL2010/000795
§ 371 (c)(1),
(2), (4) Date: Apr. 3, 2012

(87) PCT Pub. No.: WO2011/042895
PCT Pub. Date: Apr. 14, 2011

(65) Prior Publication Data
US 2012/0197135 A1    Aug. 2, 2012

Related U.S. Application Data

(60) Provisional application No. 61/291,943, filed on Jan. 4, 2010.

(30) Foreign Application Priority Data

Oct. 11, 2009   (IL) .......................................... 201369

(51) Int. Cl.
*A61B 18/18*   (2006.01)
*A61B 19/00*   (2006.01)
(Continued)

(52) U.S. Cl.
CPC ................ *A61B 18/203* (2013.01); *A61N 5/01* (2013.01); *A61B 18/20* (2013.01);
(Continued)

(58) Field of Classification Search
CPC .................... A61B 18/203; A61B 2017/0015; A61B 2019/545; A61B 2018/00476; A61B 2018/00452; A61B 2018/0094; A61B 2018/2085; A61B 2019/461; A61N 5/01; A61N 2005/067; A61N 2007/0082; A61N 5/0616
USPC .......................... 606/88, 9; 600/439; 128/898
See application file for complete search history.

(56) References Cited

U.S. PATENT DOCUMENTS 5,860,967 A * 1/1999 Zavislan et al. ................... 606/9
6,758,845 B1 * 7/2004 Weckwerth et al. ............... 606/9
(Continued)

FOREIGN PATENT DOCUMENTS

EP    1923014       5/2008
JP    2009-153606   7/2009
(Continued)

OTHER PUBLICATIONS

International Search Report and the Written Opinion Dated Feb. 24, 2011 From the International Searching Authority Re. Application No. PCT/IL2010/000795.
(Continued)

*Primary Examiner* — Long V Le
*Assistant Examiner* — Helene Bor

(57) ABSTRACT

A device of guiding a multiple area dermatologic care process. The device comprises a carrier which supports a drive of a dermatologic care tool over a skin area while the dermatologic care tool intermittently performs a plurality of dermatologic care sessions each in one of a plurality of skin subareas of the skin area and a brake unit which regulates a movement of the carrier from a first skin subarea to a second skin subarea during the drive of the dermatologic care tool.

23 Claims, 18 Drawing Sheets

(51) Int. Cl.
  *A61B 8/00* (2006.01)
  *A61B 18/20* (2006.01)
  *A61N 5/01* (2006.01)
  *A61B 18/00* (2006.01)
  *A61N 5/06* (2006.01)
  *A61N 5/067* (2006.01)
  *A61N 7/00* (2006.01)

(52) U.S. Cl.
  CPC ............... *A61B 2018/00452* (2013.01); *A61B 2018/00904* (2013.01); *A61B 2018/2085* (2013.01); *A61B 2019/461* (2013.01); *A61N 5/0616* (2013.01); *A61N 2005/067* (2013.01); *A61N 2007/0082* (2013.01)

(56) References Cited

U.S. PATENT DOCUMENTS

| | | | |
|---|---|---|---|
| 7,951,138 B2* | 5/2011 | Whitaker et al. | 606/9 |
| 8,157,807 B2* | 4/2012 | Ferren et al. | 606/88 |
| 8,182,473 B2* | 5/2012 | Altshuler et al. | 606/9 |
| 8,291,913 B2* | 10/2012 | Eimerl et al. | 128/898 |
| 8,337,407 B2* | 12/2012 | Quistgaard et al. | 600/439 |
| 2003/0069567 A1* | 4/2003 | Eckhouse et al. | 606/9 |
| 2010/0241109 A1* | 9/2010 | Floessholzer et al. | 606/9 |

FOREIGN PATENT DOCUMENTS

| | | |
|---|---|---|
| WO | WO 2009/037641 | 3/2009 |
| WO | WO 2009/104530 | 8/2009 |

OTHER PUBLICATIONS

Office Action Dated Aug. 7, 2012 From the Israel Patent Office Re. Application No. 201369 and Its Translation Into English.

International Preliminary Report on Patentability Dated Apr. 19, 2012 From the International Bureau of WIPO Re. Application No. PCT/IL2010/000795.

Office Action Dated Feb. 27, 2014 From the Israel Patent Office Re. Application No. 201369 and Its Translation Into English.

\* cited by examiner

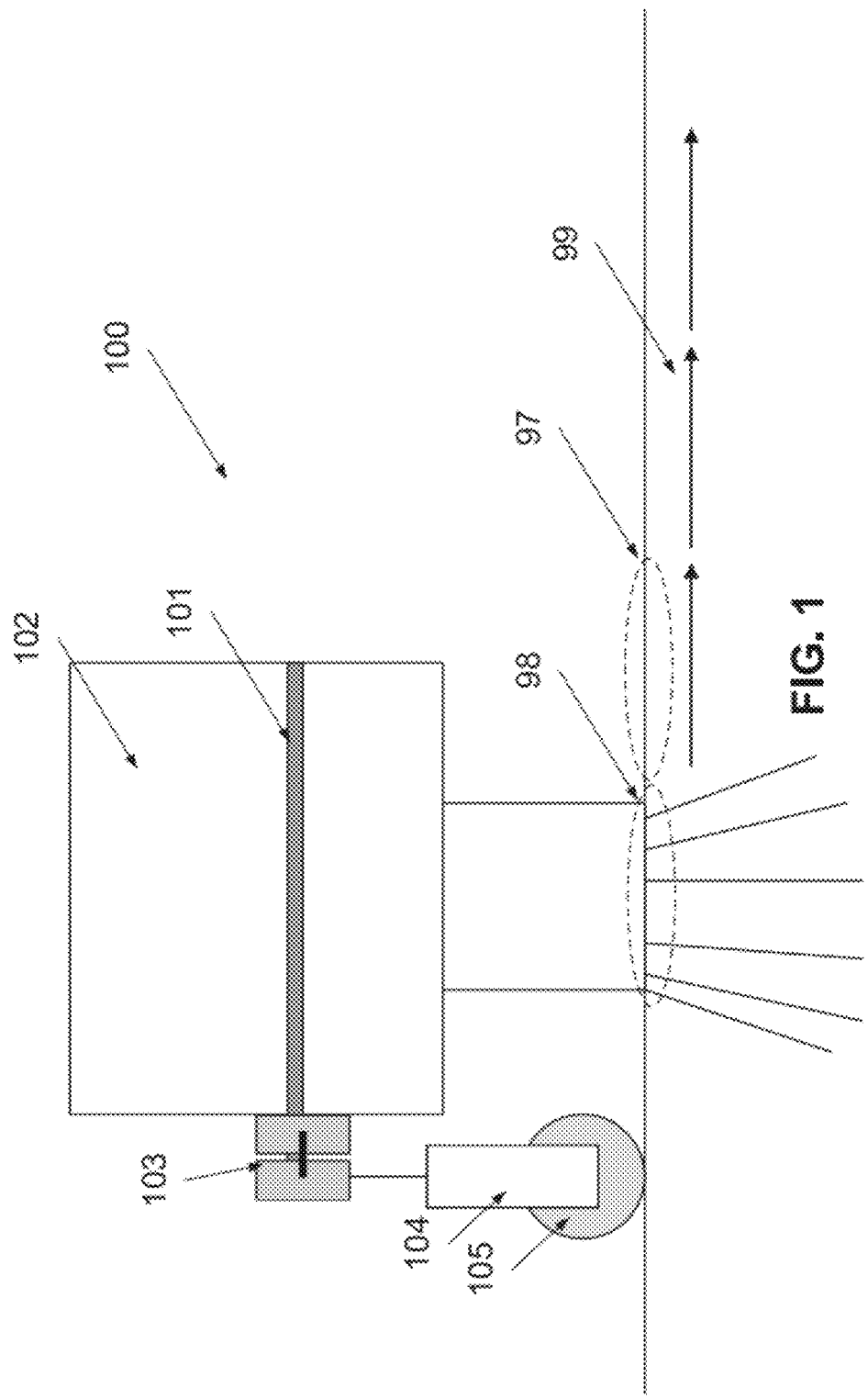

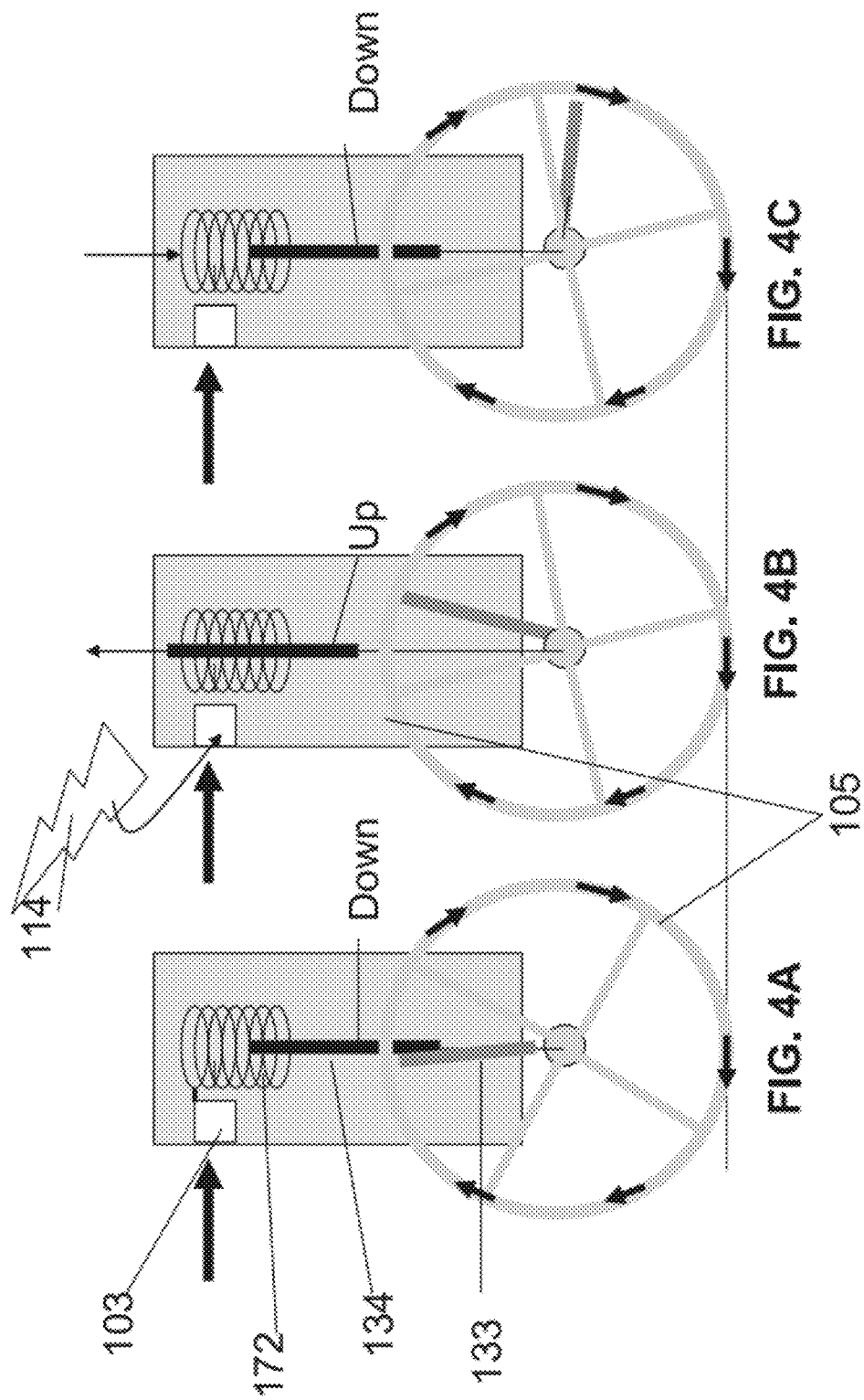

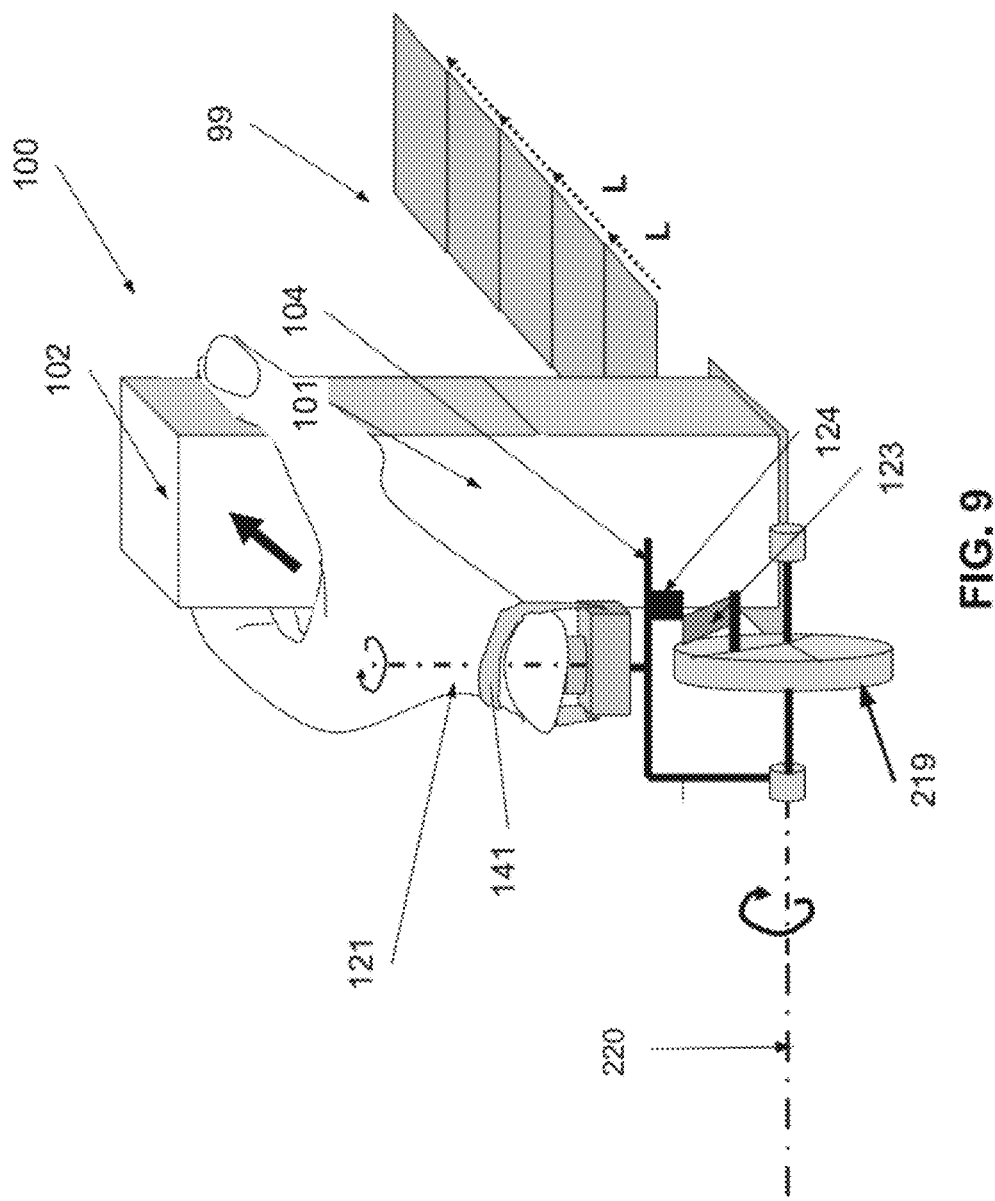

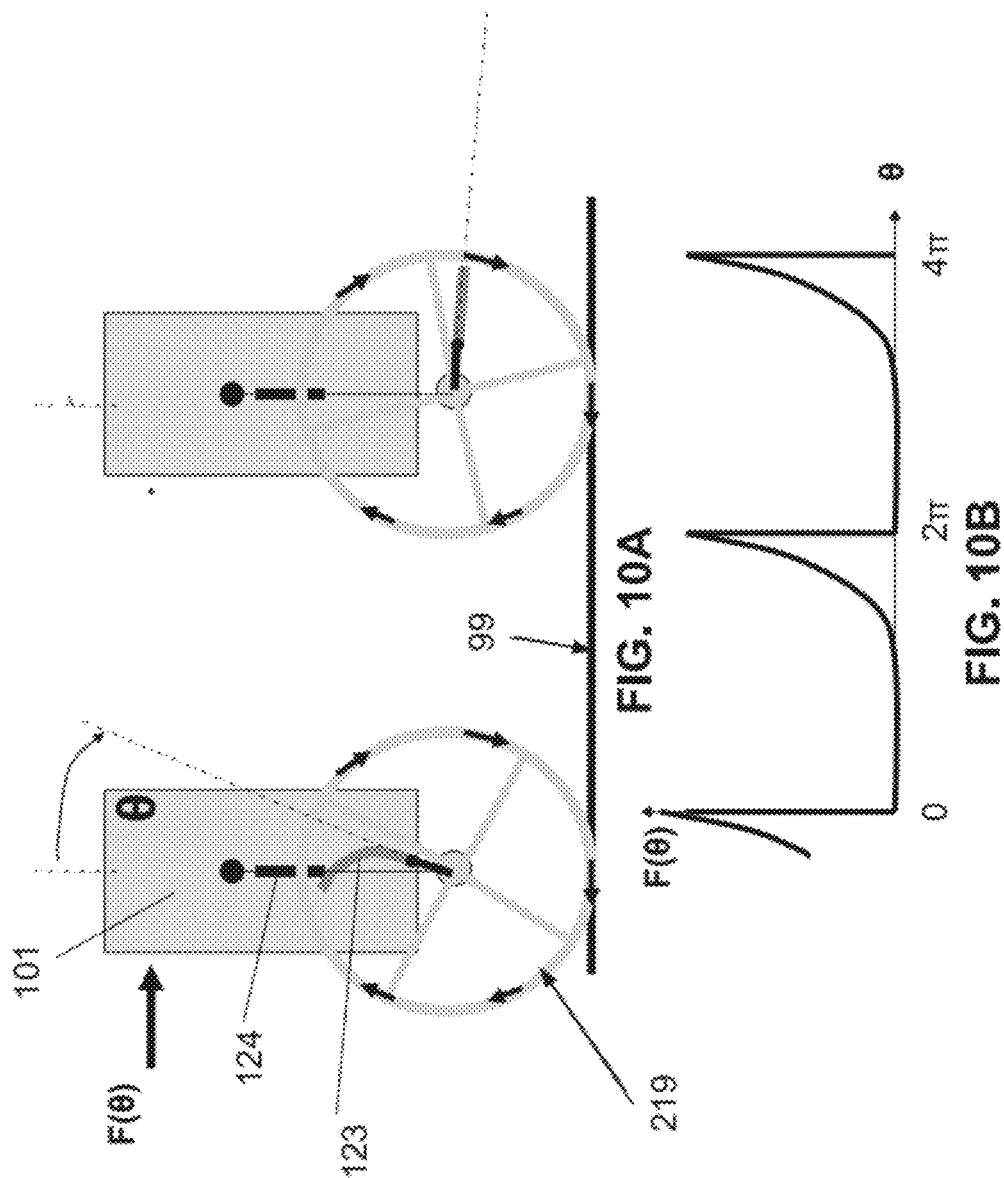

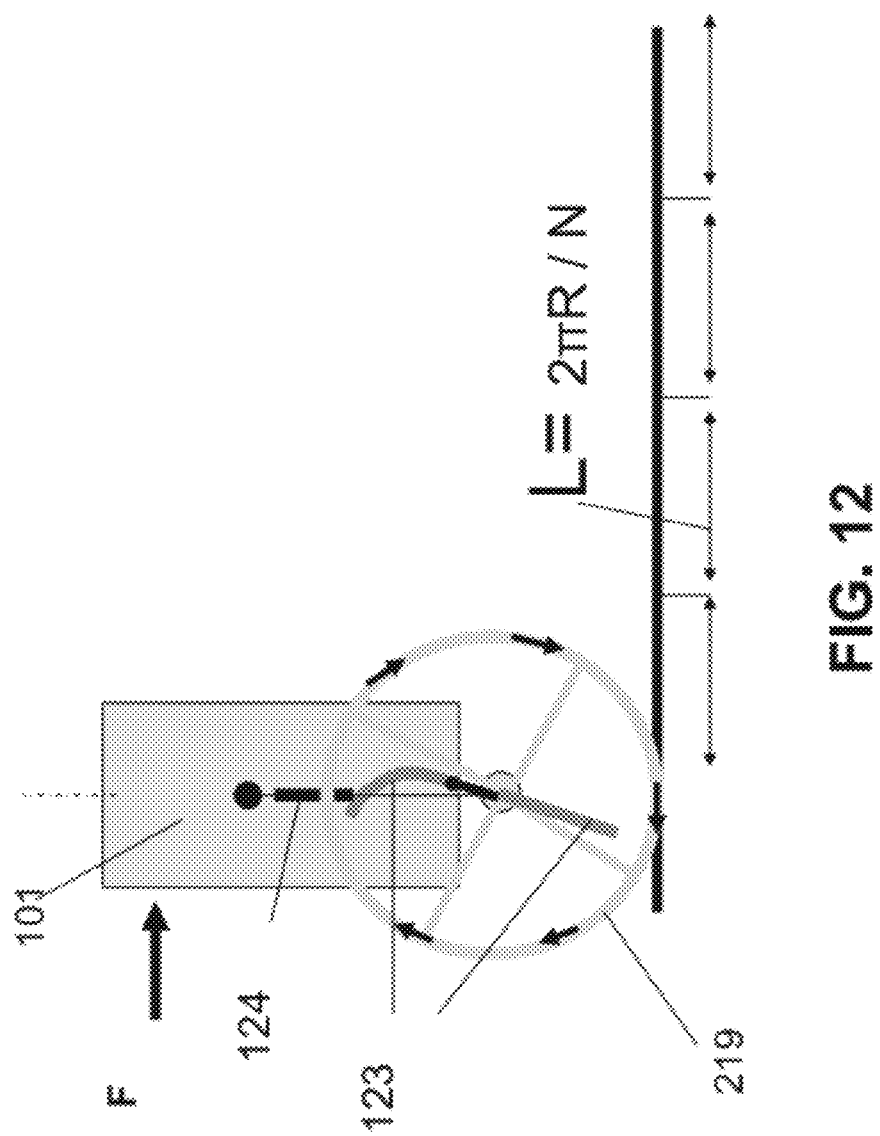

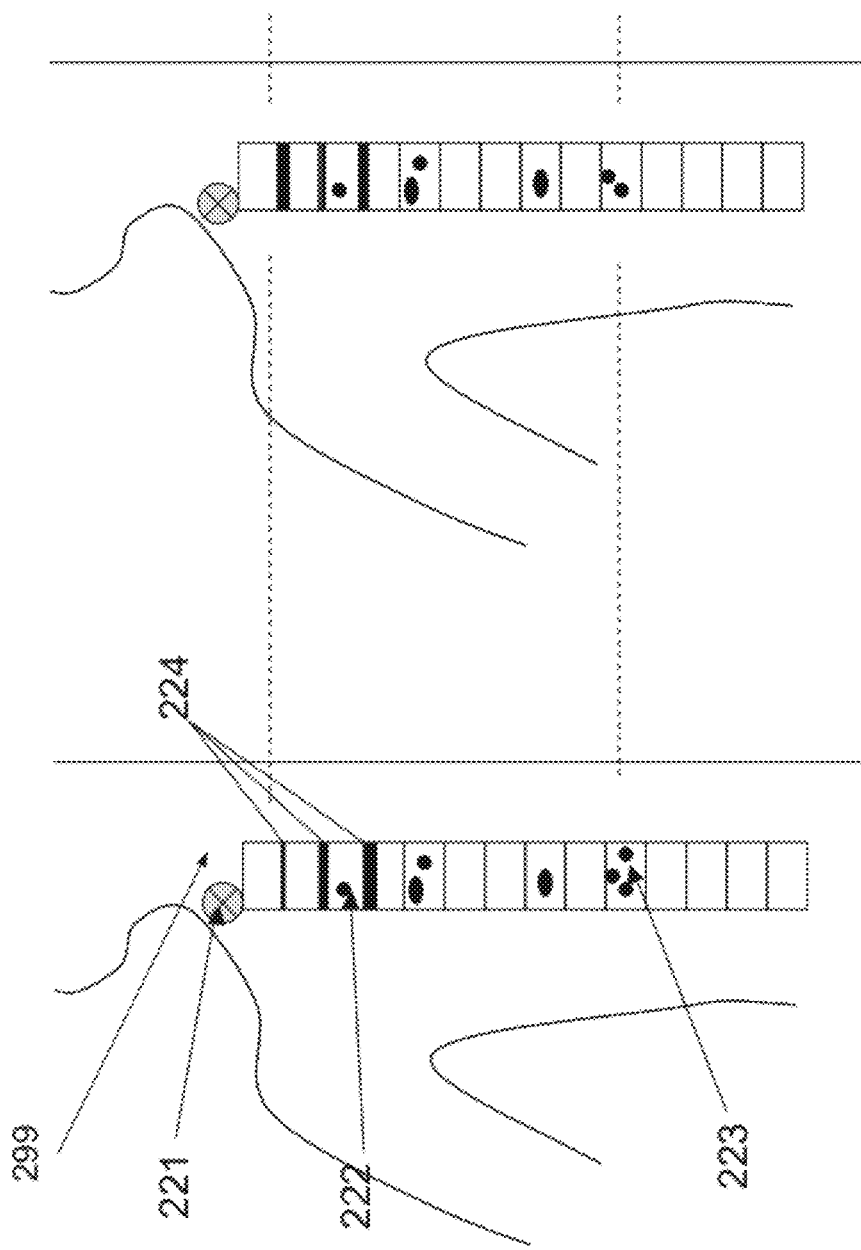

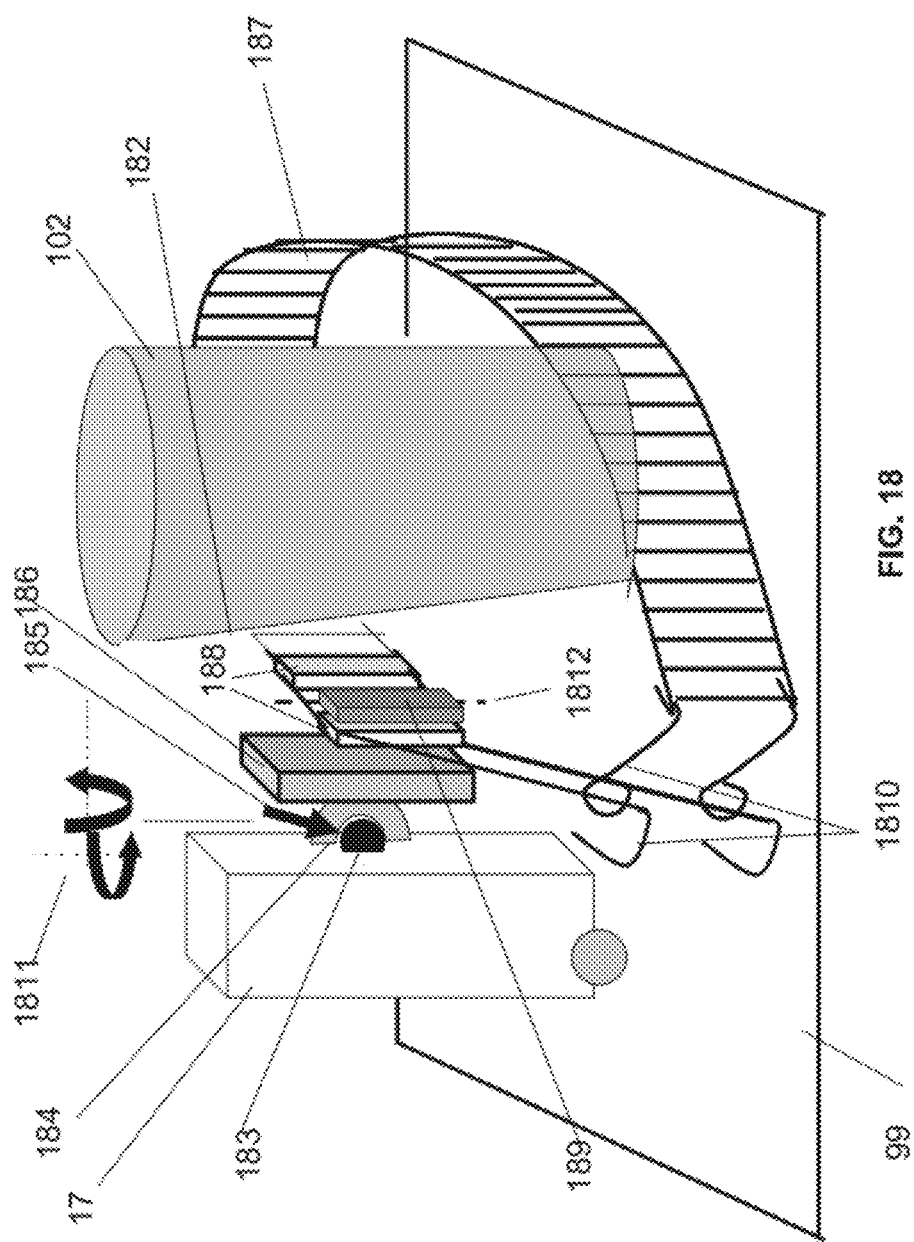

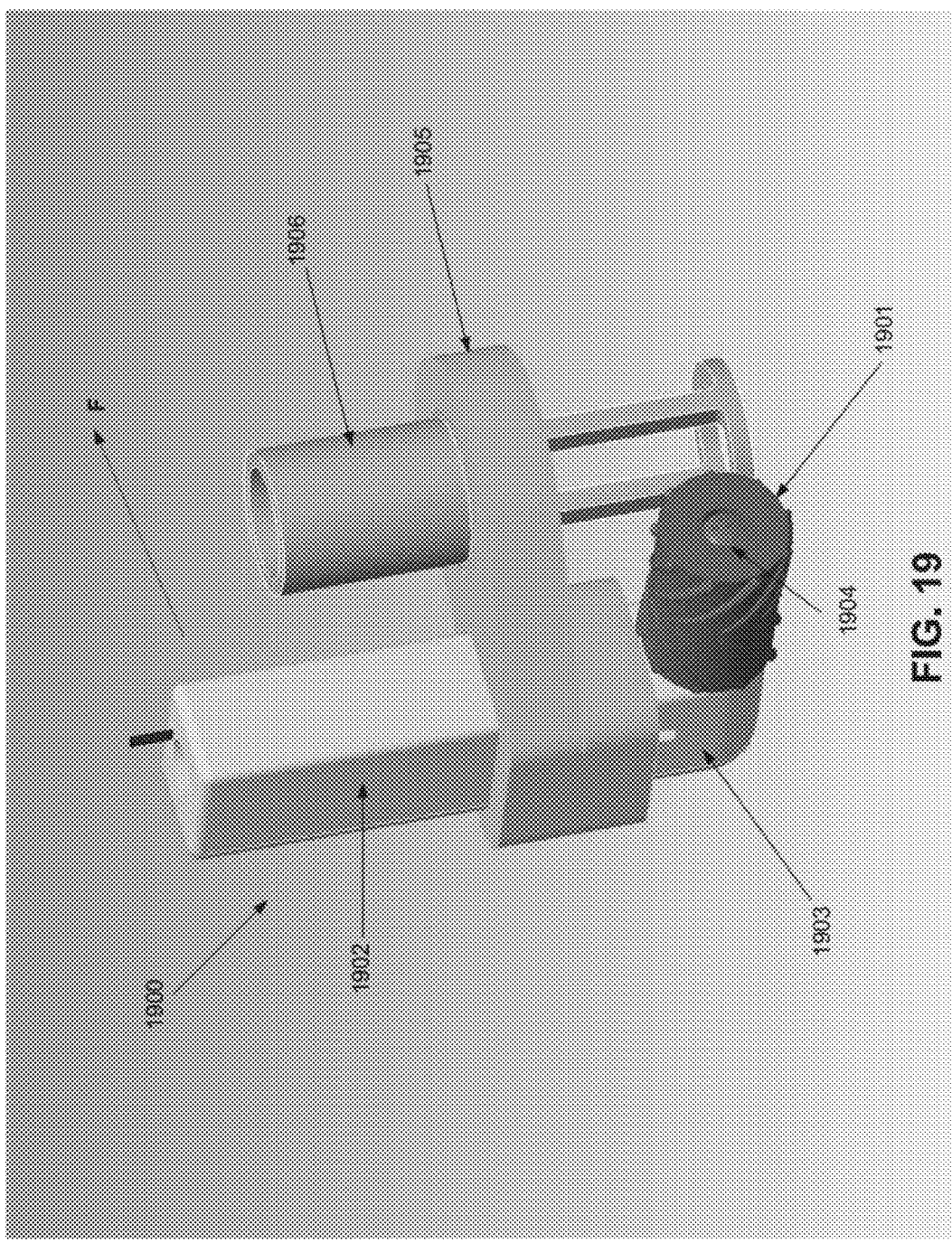

DEVICE FOR INTERMITTENTLY PERFORMING CARE SESSIONS TO FORM A LARGE SKIN AREA CARE

RELATED APPLICATIONS

This application is a National Phase of PCT Patent Application No. PCT/IL2010/000795 having International filing date of Oct. 3, 2010, which claims the benefit of priority of Israel Patent Application No. 201369 filed on Oct. 11, 2009 and U.S. Provisional Patent Application No. 61/291,943 filed on Jan. 4, 2010. The contents of the above applications are all incorporated herein by reference.

FIELD AND BACKGROUND OF THE INVENTION

The present invention, in some embodiments thereof, relates to method and system of large skin area treatments and, more particularly, but not exclusively, to method and system guiding and/or controlling a device and/or a process for large skin area treatments, such as cosmetic and/or diagnostics treatments.

In order to improve the efficacy, safety, predictability and/or tolerability of large skin area treatments, examination and/or diagnostic processes, a methodological scanning pattern has to be adopted. Such a pattern allows dividing the time spent on each portion of the large skin area in substantially equal manner, avoiding overlapping treatment sessions, and/or reducing the time span of an average treatment session.

Examples for large skin area examination and/or diagnostic processes include dermascope inspection, skin cancer inspection, and/or any other dermatologic diagnostic process. Examples for large skin area treatments include treatments based on electromagnetic waves, such as RF sources or light and ultrasound waves, for example acne treatments, hair removal treatments, tanning treatments, psoriasis treatments, skin tightening treatments, treatment of pigmented lesions, tattoo and/or any other tissue treatment.

During the last years, different methods and systems have been developed. For example U.S. Pat. No. 7,282,047 filed on Feb. 4, 2003 describes a device for moving a therapeutic energy source over an area to be treated including at least one therapeutic energy source adapted to produce therapeutic energy and coupled to a mounting structure, and at least one moving unit connected to the mounting structure and adapted to move the mounting structure and the energy source coupled thereto over an area to be exposed to therapeutic energy.

Another example is described in U.S. Pat. No. 6,758,845, filed on Oct. 8, 1999 that describes a laser skin treatment apparatus includes a handpiece for delivering laser-radiation pulses from a laser to an area of skin being treated. The area being treated is larger than an area treatable in a single firing of the laser. The larger area is treated by treating adjoining sub-areas within the larger area by repeated firings of the laser. The laser is fired automatically depending on the position of the handpiece in the larger area. Several arrangements for determining the position of the handpiece are disclosed. These include optical detection by the handpiece of indicia drawn on the skin being treated; optical, magnetic, or mechanical detection of indicia on a separate guide for the handpiece or on a roller attached to the handpiece; and detection by determining time of travel of signals from a transponder in the handpiece to a fixed reference plane.

SUMMARY OF THE INVENTION

According to some embodiments of the present invention there is provided a device of guiding a dermatologic care process in multiple skin areas. The device comprises a carrier which supports a drive of a dermatologic care tool over a skin area while the dermatologic care tool intermittently performs a plurality of dermatologic care sessions each in one of a plurality of skin subareas of the skin area and a brake unit which regulates a movement of the carrier from a first of the plurality of skin subareas to a second of the plurality of skin subareas during the drive.

Optionally, the dermatologic care tool is selected from a group consisting of: a handheld episcope, an image sensor, a camera, a video camera, a tactile treatment tool, an electromagnetic energy (EM) transmitter, a conduit of such EM pulses, an ultrasound transmitter, an intense pulsed light (IPL) epilator, and a laser tool.

More optionally, the dermatologic care tool is at least one of a head and a handpiece of any member of the group.

Optionally, the drive is manually brought up by a human operator; the brake unit regulates the movement by changing a resistance to the drive.

Optionally, the carrier is sized and shaped to for detachably and alternately support a plurality of different dermatologic care tools.

Optionally, the device further comprises detector which detects at least one of the start and end of each the dermatologic care session, the brake unit regulates the movement according to the detection.

More optionally, the dermatologic care tool performs each the dermatologic care session by emitting at least one pulse of light, the detector is a light detector that detects the at least one of the start and end of each the dermatologic care session by detecting the at least one pulse.

Optionally, the skin area is a member of group consisting of at least 60% of the skin area of a limb, at least 60% of the skin area of the abdomen, at least 60% of the skin area of the back.

Optionally, the brake unit comprises at least one wheel operatively connected to the carrier and adapted to rotate during the movement and at least one wheel brake which restrains a rotation freedom of the at least one wheel during the movement.

Optionally, the device further comprises a movement tracker which indicates a distance traveled by the carrier over the skin area. The brake unit regulates the movement according to the distance.

More optionally, the at least one wheel brake comprises at least one wheel plate connected to the wheel and a moveable plate, the at least one wheel brake restrains the rotation freedom by moving the moveable plate to collide with the at least one wheel plate during the movement.

More optionally, the at least one wheel brake comprises at least one wheel plate connected to the inner side of a rim of the wheel and a moveable element connected to a shaft of the wheel, the at least one wheel brake restrains the rotation freedom by moving the moveable element to collide with the at least one wheel plate during the movement.

More optionally, the at least one wheel brake comprises at least one wheel plate connected to the wheel and a frame plate connected to the carrier, the plates being placed so as to collide with one another during the movement and to bend at least one of the plates, the bending restrain the movement.

More optionally, the at least one wheel brake comprises at least one spherical element which is linearly actuated, for example by a spring which bulges it out of a recess. In such a manner, the spherical element is intermittently placed to collide with a bar one the wheel during its movement to restrain the movement of the device.

Optionally, the device further comprises a handle for allowing an operator to manually driving the carrier so as to perform the movement.

Optionally, the device further comprises a hand fixation element that fixes the operator's arm in relation to the device during the movement.

Optionally, the device further comprises a learning module for learning a pattern of the plurality of dermatologic care sessions; the brake unit performs the regulating according to the pattern.

Optionally, the dermatologic care tool comprises an image sensor and a flash device, the brake unit regulates the movement so that the flash device flashes when the dermatologic care tool being above one of the plurality of skin subareas.

Optionally, the device further comprises a light detector that detects the flashing; the brake unit regulates the movement according to the detection.

Optionally, the carrier is a housing comprising the components of the dermatologic care tool.

Optionally, the movement is performed in two dimensions.

Optionally, the device further comprises a strapping mechanism for clasping the dermatologic care tool to the carrier.

Optionally, the strapping mechanism comprises a segmented bracelet having a flexible layer, the flexible layer being compressed when the segmented bracelet clasps the tool.

Optionally, the carrier is in contact with the skin area.

According to some embodiments of the present invention there is provided a method of guiding a dermatologic care process. The method comprises mounting a dermatologic care tool in a carrier having a brake unit, using the carrier for supporting a drive of the dermatologic care tool over a skin area while intermittently performing a plurality of dermatologic care sessions each in one of a plurality of skin subareas of the skin area, and operating the brake unit to regulate automatically a movement of the carrier over the skin area, from one of the plurality of skin subareas to another.

Optionally, the drive is manually brought up by a human operator; the operating comprises changing the resistance to the drive.

Optionally, the skin area covers at least 60% of a member of a group consisting of a limb, the abdomen and the back of a patient.

More optionally, the method further comprises capturing an image of one of the plurality of skin subareas in each the care session.

More optionally, the method further comprises emitting an electromagnetic (EM) pulse on a different subarea of the plurality of skin subareas in each the care session.

Optionally, the EM pulse is selected from a group consisting of a pulsed laser beam, an infrared light pulse, and an ultrasound pulse.

More optionally, the method further comprises applying a tactile stimulation on a different subarea of the plurality of skin subareas in each the care session.

More optionally, the method further comprises detecting at least one of the start and end of each the dermatologic care session during the movement, the operating being performed according to the detecting.

Optionally, the regulating is performed according to distance traveled by the carrier during the movement.

More optionally, the method further comprises learning a rate of the plurality of dermatologic care sessions and operating the brake unit according to the rate.

According to some embodiments of the present invention there is provided a method of guiding a dermatologic care process. The method comprises supporting a drive of a dermatologic care tool over a skin area of a patient, automatically detecting a plurality of electromagnetic pulses intermittently emitted by the dermatologic care tool by at least one light detector, and operating a brake unit according to the plurality of electromagnetic pulses to regulate the drive.

Optionally, the light detector is externally attached to the dermatologic care tool.

More optionally, the method further comprises capturing a plurality of images of a plurality of subareas of the skin area during the drive and outputting the plurality of images for diagnosis.

More optionally, the method further comprises marking an initial location on the skin area before the drive and using the initial location for performing an additional drive in a respective manner to the method to acquire an plurality of additional image so that each the image having a respective additional image of substantially the same subarea.

More optionally, the method further comprises supporting a second drive of the dermatologic care tool over the skin area in a later period, automatically detecting a plurality of additional electromagnetic pulses intermittently emitted by the dermatologic care tool by the at least one light detector; and operating the brake unit according to the plurality of additional electromagnetic pulses to regulate the drive and capturing a plurality of additional images of the plurality of subareas during the additional drive and simultaneously presenting the plurality of images and the plurality of additional images.

Optionally, the brake unit is externally attached to the dermatologic care tool.

According to some embodiments of the present invention there is provided a method of guiding a dermatologic care process in multiple skin areas. The method comprises supporting a drive of a dermatologic care tool over a skin area of a patient while the dermatologic care tool performs a plurality of dermatologic care sessions, automatically estimating a distance traveled by the dermatologic care tool during the drive, and an operating brake unit to regulate the drive according to the distance.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of a device of guiding a dermatologic care tool that performs a multiple area dermatologic care process for examining, diagnosing and/or treating a large skin area, according to some embodiments of the present invention;

FIGS. 4A-4C are a series of schematic illustrations of a brake unit connected to a light detector, according to some embodiments of the present invention;

FIG. 9 schematically depicts a device with a carrier that is physically connected to a strapping mechanism that fixes the hand of the operator in relation to the device, according to some embodiments of the present invention;

FIG. 10A is a schematic illustration of an exemplary wheel with a rotating extension having a bending angle θ, according to some embodiments of the present invention;

FIG. 10B is an exemplary graph where that depicts the resistance applied on the wheel in response to the bending angle exemplified in FIG. 10A, according to some embodiments of the present invention;

FIG. 12 is a schematic illustration of a brake unit where a number of extensions are attached to a wheel so as to collide with a frame extension a number of times each full rotation of the wheel, according to some embodiments of the present invention;

FIGS. 17A and 17B are schematic illustration of torso and a set of proximate skin subareas which are sequentially imaged by the device depicted in FIG. 16 in two different periods, according to some embodiments of the present invention; and FIG. 18 is a schematic illustration of a strapping mechanism for fastening various dermatologic care tools, according to some embodiments of the present invention.

FIG. 19 is a schematic illustration of a device with a mechanism for replacing detachable intermittent advance rollers in a large variety of sizes and shapes which are adapted to guide different dermatologic care tools, on slippery wet skin as well as on dry skin, according to some embodiments of the present invention.

DESCRIPTION OF EMBODIMENTS OF THE INVENTION

Figure 2A:
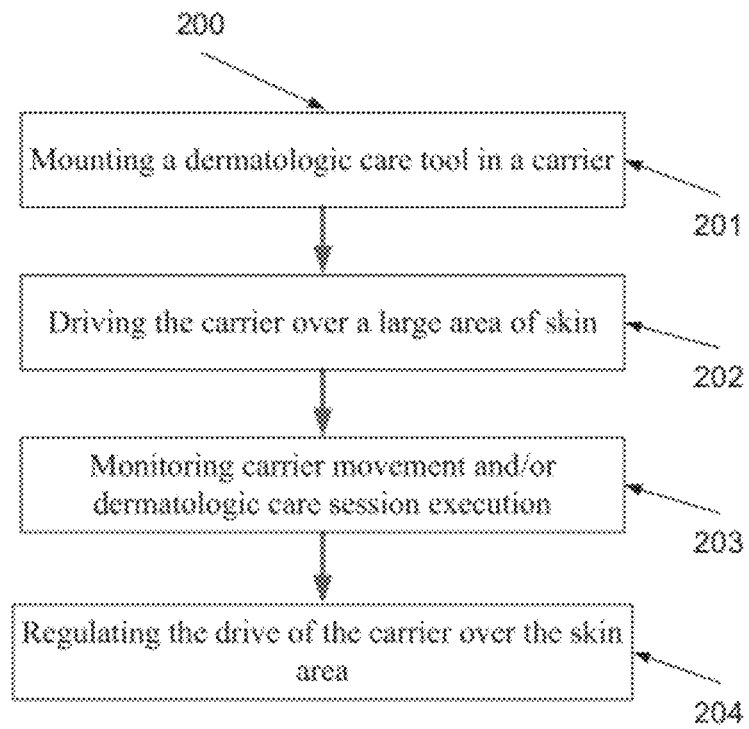
FIG. 2A is a flowchart of a method of guiding a multiple area dermatologic care process, according to some embodiments of the present invention.

The present invention, in some embodiments thereof, relates to method and system of large skin area treatments and, more particularly, but not exclusively, to method and system guiding and/or controlling a device and/or a process for large skin area treatments, such as cosmetic and/or diagnostics treatments.

According to some embodiments of the present invention there is provided a method and a device for guiding a multiple area dermatologic care process performed over a large skin area, such as a limb, the back and the abdomen, by using a brake unit for regulating the drive of a dermatologic care tool over the large skin area. The dermatologic care tool may be a common handpiece of a hair removal system or any other dermatologic care system and/or a camera used to capture images of pigmented lesions for diagnosis. The dermatologic care tool may be manually driven, for example by a human operator that holds the dermatologic care tool or automatically driven, for example by a robotic arm.

The device includes a carrier that supports the manual or automatic drive of the dermatologic care tool over the skin area while the dermatologic care tool intermittently performs a plurality of dermatologic care sessions, each in one of the subareas of the skin area. The carrier may be sized and shaped to support a specific dermatologic care tool and/or include adjustable elements that allow it to support a number of different dermatologic care tools. A dermatologic care session may be an epilation session in which the subarea is radiated with electromagnetic (EM) radiation, for example an intense pulsed light (IPL) beam a laser beam or other skin treatment sessions with IPLs, lasers, ultraviolet sources or radio frequency monopolar or bipolar treatment current and/or ultrasonic waves. In another example, a dermatologic care session may be a diagnostical session in which an image of the subarea is taken for diagnosis and/or displayed for real time examination of a physician or another caretaker. The device further includes a brake unit that regulates the movement of the carrier between the skin subareas, which are optionally touching one another. In such a manner, the brake unit assists in pacing the process and in avoiding overtreating the skin area by avoiding overlapping treatment subareas or unintentionally skipping over areas which should be treated. Such a regulation reduces the amount of attention and/or effort that the operator is required to put in the multiple area treatment process.

It should be noted that the device may be seen as a unit which operates a brake mechanism (release) according to a signal from a dermatologic care tool without controlling and/or changing the modus operandi of the dermatologic care tool. In such embodiments, the carrier of the device is set to support virtually any dermatologic care tool and so that the device works without any adjustment or integration with the dermatologic care tool. This is different from known device specific intermittent advance devices which are set to control a specific dermatologic care tool by monitoring location and/or position on the body of the patient and sending a specific triggering signal to the specific dermatologic care tool to trigger an illumination cycle.

Optionally, the device includes a detector for detecting the performance, the initiation, and/or the ending of the dermatologic care sessions. In such embodiments, the brake unit regulates the drive of the dermatologic care tool according to the pace in which it performs the dermatologic care sessions. For example, the detector may be a light detector that detects when the dermatologic care tool emits light towards the skin area, an indication that a dermatologic care session has been performed and the device should be repositioned over another skin subarea to proceed with the multiple area dermatologic care process.

Additionally or alternatively, the device includes a mechanical and/or an electronic movement assembly which prevents or makes difficult moving the carrier 101 a distance larger than a preselected distance over the skin area, for example from the center of one skin subarea to another. In such embodiments, the brake unit regulates the movement of the carrier according to a movement tracker. An exemplary mechanical movement stopping mechanism may be based on a bulging element in a rotation of a wheel that rotates during the drive of the device.

According to some embodiments of the present invention there is provided a method of guiding a dermatologic multiple area care treatment according to the distance a dermatologic care tool traveled over the skin area. The method is based on supporting a drive of a dermatologic care tool over a skin area of a patient while the dermatologic care tool performs a plurality of dermatologic care sessions, for example as outlined above and described below. This supporting allows automatically estimating a distance traveled by the dermatologic care tool during the drive, for example using a movement indicator and an operating brake unit to regulate the drive according to the distance.

According to some embodiments of the present invention there is provided a method of guiding a multiple area dermatologic care process according to the detection of electromagnetic pulses emitted during the performance of dermatologic care sessions. The method is based on supporting a drive of a dermatologic care tool over a skin area of a patient, automatically detecting a plurality of electromagnetic pulses intermittently emitted by the dermatologic care tool by at least one electromagnetic radiation detector such as a light detector which detects a scattered portion of the treatment light, and operating a brake unit according to the electromagnetic pulses to regulate the drive.

According to some embodiments of the present invention, the device 100 regulates the intermittent advance of the diagnostic or treatment device and does not control or activate a treatment and/or a diagnostic tool but is rather controlled and/or activated by the operation of the treatment and/or diagnostic tool. The device controls the maneuvering of the diagnostic and/or treatment tool over the treatment area as the brake unit 104 changes the resistance to the driving of the device 200 over the skin area. The resistance change indicates and/or forces the operator to wait until a treatment pulse is emitted by tool and then indicates and/or allows the operator to drive the tool to another skin subarea. As a result, the device may be used for guiding various tools with different operation patterns, programs and/or hardware.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic illustration of a device 100 of guiding a dermatologic care tool that performs a multiple area dermatologic care process for examining, diagnosing and/or treating a large skin area 99, such as the back, the abdomen, and/or a limb of patient, according to some embodiments of the present invention. As used herein, a multiple area dermatologic care process is a treatment, an examination, and/or a diagnostic process is based on a plurality of sessions during which a plurality of skin subareas of a large skin area, such as the back, the abdomen, and/or a limb of patient are intermittently treated, examined, and/or a diagnosed.

The device 100 includes a carrier 101 that detachably supports a dermatologic care tool 102 that performs the dermatologic care sessions and/or a head of such a device. Optionally, the carrier 101 is a strapping belt that adjustably clamps, supports and/or otherwise attaches the multiple area dermatologic care tool or the head thereof 102. The head of the multiple area dermatologic care tool 102 may be a handpiece of treatment and/or diagnosis head or lead adjusted to be maneuvered manually and/or automatically. The multiple area dermatologic care tool 102 may be a handheld episcope dermascope and/or an image sensor, such as a complementary metal oxide semiconductor (CMOS) based detector and/or a charge coupled device (CCD) based detector adapted to capture an image of a skin portion, a camera, a video camera, a tactile treatment tool, an electromagnetic energy (EM) transmitter for generating pulses of energy delivered to the skin for clinical applications or a head or a lead of a conduit of such pulses. For example, the EM transmitter is an ultrasound transmitter for emitting ultrasound waves onto the skin, an intense pulsed light (IPL) epilator, and a laser source, for example a diode-laser array, for emitting a pulsed laser beam or any other therapeutic energy source. For brevity, a multiple area dermatologic care tool 102 means one or more of the aforementioned devices or device heads. The multiple area dermatologic care tool 102 is designed to perform each dermatologic care session in a skin subarea of the treated, examined and/or diagnosed large skin area 99, for example as shown at 98.

Optionally, the dermatologic care session is an epilation session of an IPL epilator that includes emitting full spectrum light to perform phototricholysis or photoepilation in the skin subarea 98. Optionally, the dermatologic care session includes capturing an image of the skin subarea 98 to diagnose pigmented lesions imaged therein or diagnose the condition of a skin suspected of being cancerous pathology. Optionally, the dermatologic care session is an examination session in which the multiple area dermatologic care tool 102 is a handheld episcope and/or dermascope that projects an image of the skin subarea 98 for a diagnosis of a physician or another caretaker.

The multiple area dermatologic care tool 102 repeatedly performs dermatologic care sessions in which a plurality of care sessions are held to examine, diagnose and/or treat a large skin area, such as at least 60% of the back, the abdomen, and/or a limb of a patient, optionally at least 80% of these area, for example about 100% of these areas. For example, images of skin subareas of the large skin area 99 may be captured and/or EM waves, such as one or more pulsed laser beams and/or ultrasound waves, may be emitted onto such skin subareas, during the maneuvering of the multiple area dermatologic care tool 102 on the large skin area 99. As used herein, on the large skin area means when the multiple area dermatologic care tool 102 touches the large skin area 99 or placed above the large skin area so as to examine, treat, and/or diagnose a skin subarea thereof.

Performing a number of sessions in one skin subarea or on overlapping skin segments may undesirably expose the patient to redundant radiation and/or increases the multiple area process time.

The device 100 further includes a brake unit 104 that regulates the movement of the carrier 101 and the multiple area dermatologic care tool 102 on the large skin area 99, for example from one skin subarea to another, for instance from skin subarea 98 to skin subarea 97. In such a manner, overlapping in areas treated, diagnosed or examined by the dermatologic care tool 102, for example a handpiece of a laser epilation system or an image sensor of a skin lesion diagnosing system, may be reduced or eliminated and the time which takes to examine, treat, or diagnose the large skin area 99 is reduced. The regulation may be performed by monitoring the performance, actuation, and/or operation of the dermatologic care process and/or the movement of the device 100 over the large skin area. It should be noted that the regulation is not performed as a result of the skin color or shape and/or the reaction of the skin to the performance and/or operation of the dermatologic care process and/or the movement.

Optionally, the brake unit 104 is driven, automatically and/or manually, from a skin subarea to a proximate skin subarea during an interlude between dermatologic care sessions and not during the performance of a dermatologic care session.

Additionally or alternately, the brake unit 104 regulates the movement of the carrier 101 by restraining one or more movement elements during a dermatologic care session or a period, for example about 0.1, 0.5, 1, 2, 4, 8, and 15 seconds, before the initiation thereof.

For example, as shown at FIG. 1, the brake unit 104 includes a wheel 105. However, the brake unit 104 may include a number of wheels one or more one or more rollers, and/or balls, which are operatively connected to the carrier 101 and adapted to rotate or roll when the carrier is moved over the skin of the patent. In such embodiments the brake unit 104 further includes one or more wheel brakes which restrain the rotation or rolling freedom of the one or more wheels, rollers, and/or balls according to the outputs of the detector. For example, the brake unit 104 may restrain, partly or entirely, the rotation or rolling of the one or more wheels, wheels and/or balls, according to the outputs of the detector of performance of 102. Such a restrain changes the resistance to the driving of the device 200 over the skin area.

It should be noted that the device 100 may be integrally formed into a dermatologic care tool 102, such a head of a hair removal system or a camera which is used to capture images of lesion for manual or automatic diagnosis. In such embodiment, the carrier 101 may be replaced by a housing that includes or attached to the components of the dermatologic care tool 102 and the device 100.

Reference is now also made to FIG. 2A, which is a flowchart of a method of guiding a multiple area dermatologic care process, according to some embodiments of the present invention. The method allows guiding the pace in which the device 100 is guided over the skin area 99 and/or the velocity of the device.

First, as shown at 201, the dermatologic care tool 102 is placed in the carrier 101. Optionally, the operator selects the dermatologic care tool 102 from a plurality of possible dermatologic care tools 102 which are available thereto. For example, when the multiple area process is an epilation process of a large skin area, an epilator head is mounted in the carrier. In another embodiment, the operator may mount a dermatologic care tool that includes one or more image sensors for the diagnosis of pigmented lesions. Optionally, the carrier 101 is attached to the dermatologic care tool 102 by changing the perimeter of one or more adjustable strap and/or bands.

Now, as shown at 202, the carrier 101 with the dermatologic care tool 102 is driven, for example glided, over a large skin area while the dermatologic care tool performs a multiple area process each in one of a plurality of skin subareas of the large skin area.

Figure 3A:
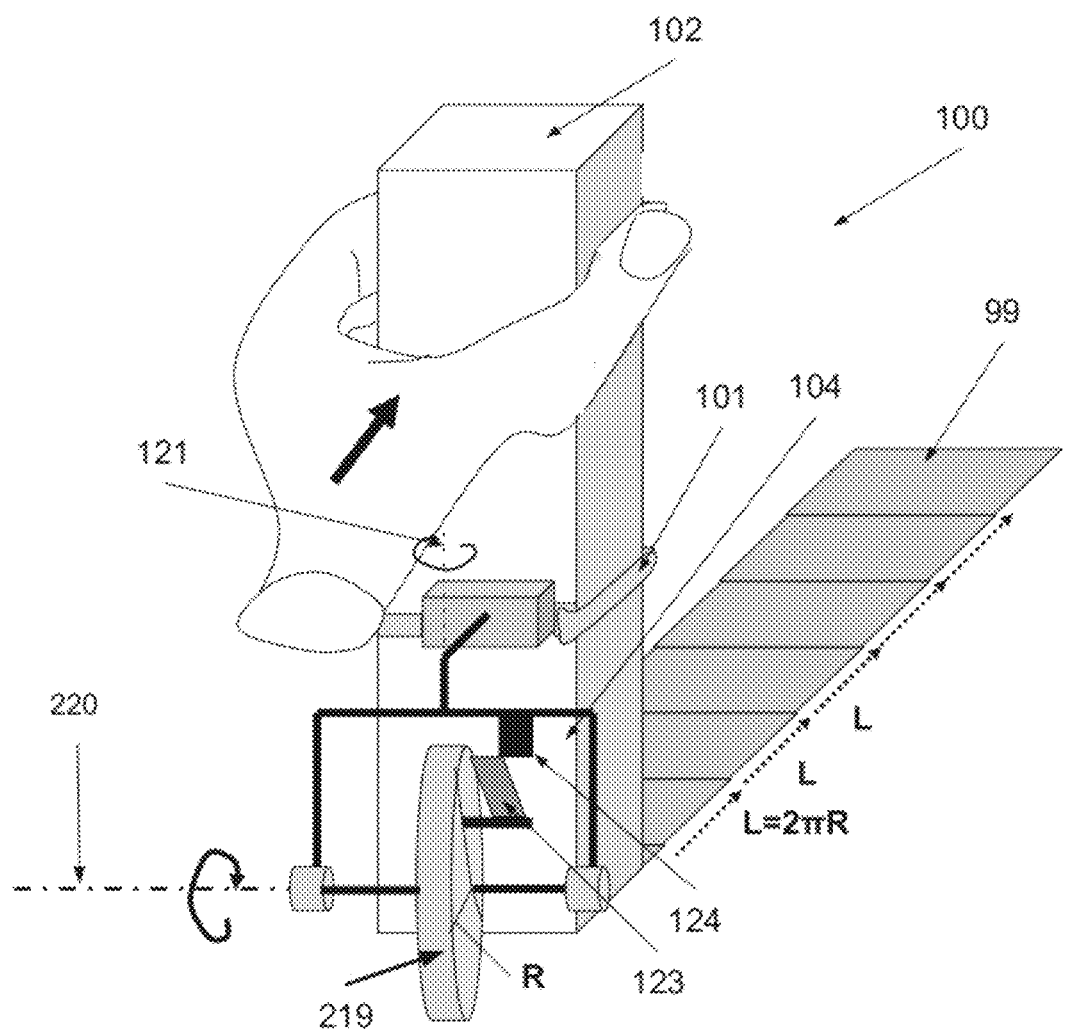
FIG. 3A is a schematic illustration of a device designed to be manually maneuvered, for example pushed, by the operator, according to some embodiments of the present invention.

According to some embodiments of the present invention, the carrier 101 and the dermatologic care tool 102 are manually maneuvered, for example pushed, by the operator. For example, as shown in FIG. 3A, the operator may drive the dermatologic care tool 102 along a path on the skin 99 of the patient. Optionally, the carrier 101 and the wheel 219 depicted in FIG. 3A allow rotating the dermatologic care tool 102 around a central axis 121. The carrier 101 may allow driving the supported dermatologic care tool 102 in a direction along a line parallel to the plane of the wheel 219, while enabling gradual change of direction with the aid of central axis 121, over the patient's skin and/or limit the orientation thereof to certain trajectories. Such a limitation may be applied by locking the rotation and/or rolling of one or more wheels, wheels, and/or balls in one or more directions.

According to some embodiments of the present invention, the carrier 101 with the dermatologic care tool 102 is automatically maneuvered, for example by a robotic hand and/or an actuation means that is operatively attached thereto, for example a set of wheels and the like.

During the driving of the dermatologic care tool 102 over the skin of the patient, a plurality of dermatologic care sessions are preformed, for example as described above.

As shown by 203, the movement of the carrier 101 and/or the execution of dermatologic care process are monitored during the actuation of the carrier over the skin. This monitoring allows regulating the driving of the dermatologic care tool over the skin area according to its actual operation and/or actuation and not according to the color and/or shape of the skin and/or the reaction of the skin to the session.

Figure 2B:
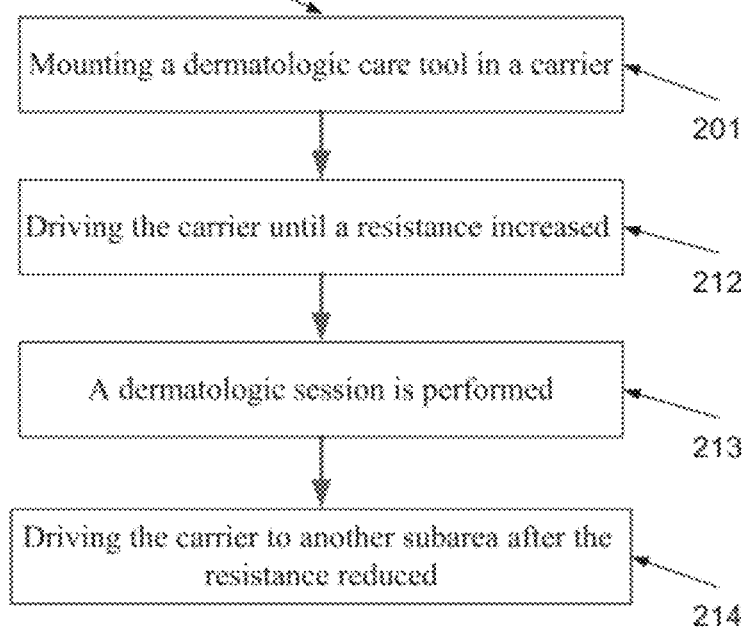
FIG. 2B is a flowchart of a method of guiding a carrier that supports a dermatologic care tool to perform a multiple area dermatologic care process, according to some embodiments of the present invention.

Accordingly, during the multiple Area dermatologic process and, as shown at 204, the movement of the carrier 101 over the skin area, from one of the skin subareas to another, is regulated, ending with a halt of movement and passively waiting for the next care execution Reference is now also made to FIG. 2B, which is a flowchart of a method 210 of guiding a carrier, such as 101, that supports a dermatologic care tool, such as 102, to perform a multiple area dermatologic care process, according to some embodiments of the present invention. Block 201 is as described above. Then, as shown at 212, the carrier 101 is driven over the subareas of the skin until the resistance which is applied by the carrier, for example by the brake unit 104 is increased. Optionally, the increased resistance stops the carrier. Now, as shown at 213, a care session is autonomously executed by the driven dermatologic care tool 102. Now, as shown at 214, the resistance applied by the carrier 101 changes so as to allow driving the dermatologic care tool 102 to a neighboring subarea, proceeding with the multiple area dermatologic care process.

According to some embodiments of the present invention, the device 100 further includes one or more detectors, referred to herein as a detector 103, which detects the initiation of a dermatologic care session, the end of the a dermatologic care session, and/or an interlude between the dermatologic care sessions. For example, the detector 103 is adjusted to detect the emission of such EM waves and/or the lack of emission of such EM waves. The detector 103 may be a light detector adapted to detect an illumination of a skin subarea, for example by measuring light reflected therefrom during an epilation session.

Figure 5:
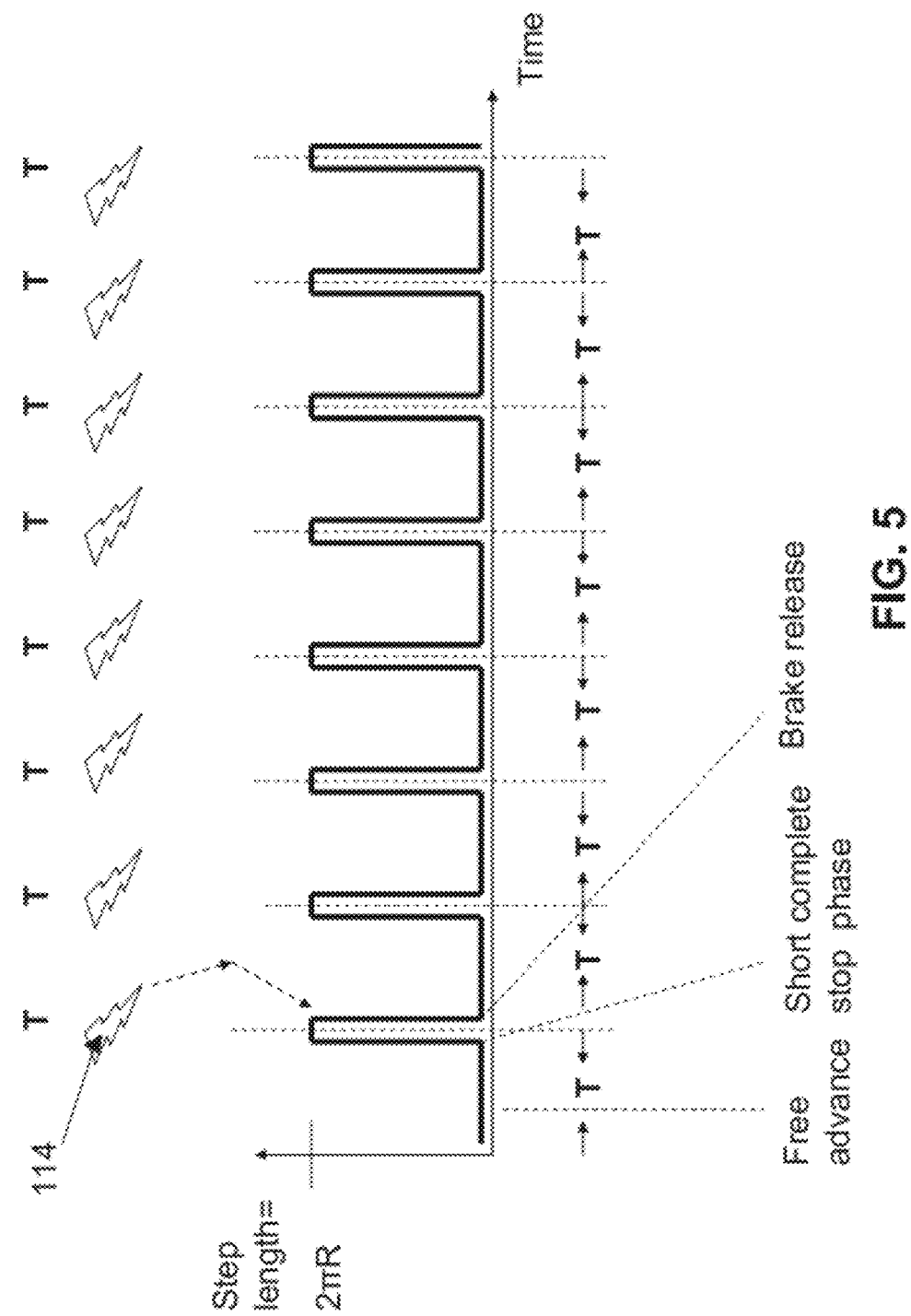
FIG. 5 is a graph that depicts a repetitive release of a plate of a wheel brake unit in synchronization with a repetitive illumination detected by a light detector, according to some embodiments of the present invention.

For example, reference is now made to FIGS. 4A-4C, which is a series of schematic illustrations of a brake unit 104 connected to a light detector 103, according to some embodiments of the present invention. The brake unit 104 is designed to be connected to a carrier 101, as shown at 101 of FIG. 1. Similarly to the described above, the wheel 105 of the brake unit 104 is in contact with the skin area when the dermatologic care tool 102 is driven thereover. The brake unit 104 includes a wheel brake that has a first plate 134 adapted to be lifted and taken down in an axis perpendicular to the movement trajectory of the carrier 101 and a second plate 133 attached to the wheel 105. The plates 133, 134 are placed in a common plane so that the second plate 133 collides into the first plate 134 when the first plate 134 is lowered, for example as shown at FIG. 4A. Optionally, plate 134 is lifted by an electromagnet 172 when a current flows through a solenoid thereof. An example of a solenoid which may be used in the current embodiment is a tubular solenoid model SDT1327L-2XX produced by NSF Controls, UK, which the specification thereof is incorporated herein by reference. When the detector 103, which is optionally a photodetector assembly, detects light 114 which is generated as a result of the autonomous execution of the skin care treatment or diagnostic, a circuit which allows a current from a power source, such as a battery, to flow through the electromagnet 172, is closed and the electromagnet lifts the plate 134, which is optionally a magnet, to allow the wheel 105 to rotate freely, as shown at FIG. 4B. This process may take no more than few milliseconds. A predetermined time following the elevation the circuit is opened and the plate 134 is taken down, optionally by gravity, as shown at FIG. 4C. This may take less than a half a second, for example about 150-200 milliseconds. This process may be repeated every time the detector 103 detects an illumination, for example as shown at FIG. 5 that is a graph that depicts a repetitive release of the plate 134 synchronized with a repetitive illumination 14 which is detected by the detector.

It should be noted that autonomous is related to dermatologic care operations which are performed by the dermatologic care tool 102 without any command, indication, measurement, and/or instruction from the device 100 or any sensor which is embodied therein.

Optionally, plate 133 is flexible, allowing the operator to move the device 100 even when plate 134 is down. This embodiment allows the operator to maneuver the device 100 in a case of failure and to avoid burning a certain skin subarea.

Figure 6:
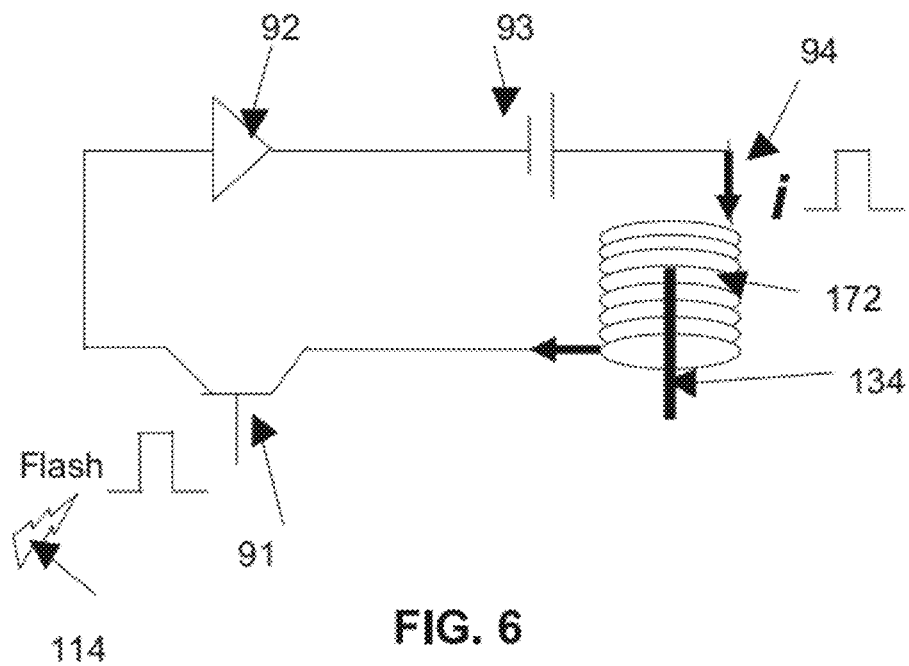
FIG. 6 is a schematic presentation of a circuit which enables a plate release when a pulsed light is emitted, according to some embodiments of the present invention.

FIG. 6 is a schematic presentation of the circuit which enables the plate 134 releases when pulsed light 114 is emitted. Similar circuits may be used for other brake systems which are triggered by a light detection. The circuit allows a current i from a battery 93 or another power source, to flow through the electromagnet 172 when a photodiode 91 detects light. When no light is detected, the flow of current is inhibited and the plate 134 is taken down. Optionally, the plate 134 is made from a rare earth metal.

Figure 7:
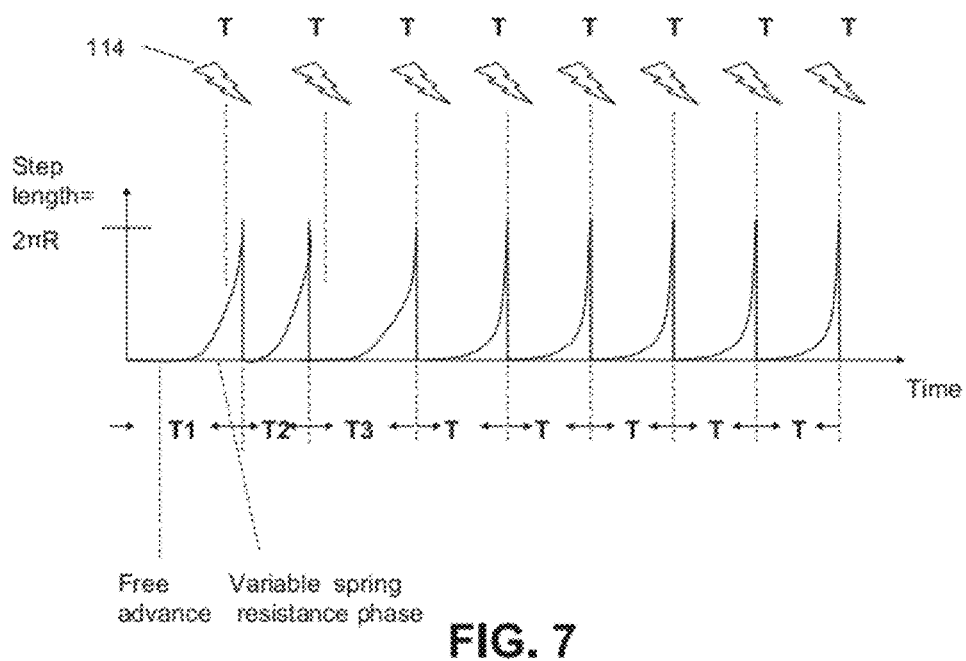
FIG. 7 schematically depicts intermittent advance of the device along the large skin area, according to some embodiments of the present invention.

Optionally, each dermatologic care session includes one or more light emissions, such as laser beam light emissions. In such embodiments, the supported dermatologic care tool 102 may include an intense pulsed light (IPL) epilator and/or a laser source, for example a diode-laser array, for emitting a pulsed laser beam. In such embodiments, the detector 103 includes a light detector that detects the excitation of the light source. FIG. 7 schematically depicts intermittent advance of the device 100 along the large skin area. Light pulses 114 are repetitively detected by the detector 103 every T seconds. The brake unit 104 regulates the movement of the carrier 101 according to the detected light pulses 114, for example by activating the wheel brakes so that a low mechanical impedance applied after a session of one or more light emissions are detected and allows free movement of carrier 101 at the termination of the care/diagnostic session, whereas a high mechanical impedance is applied when carrier 101 reaches the end of area 98 or 97 resulting in a halt of the movement.

Optionally, the brake unit 104 is calibrated according to one or more sessions which are recorded by the detector 103. For example, the brake unit 104 may calculate the interlude between two sequential sessions and time the impudence pattern accordingly. Such calibration allows estimating when a session begins and activate the brake unit 104 accordingly, for example with reference to FIG. 7, after time T1 or before time T2. When the carrier 101 is manually maneuvered, the change in the applied impedance guides the operator how to drive the device 100. Optionally, the brake unit 104 includes a learning module, such as a phase locked loop (PLL) circuit, which learns a pattern, such as a repetitive behavior, for example a rate and/or a phase, of the care sessions, for instance of repetitive flashes, and generates instructions, such as pulses, with identical behavior to control the wheel brake, for example by activating a coil and/or any other brake mechanism that may be used. Such a calibration reduces the sensitivity to variations in the intensity of the flashes, for example variations caused by a change in the position of the device on the skin, the skin reflectivity, and/or the position of the operator hand. It should be noted that when a PLL is used for regulating the device 100 the brake unit 104 does not misregulate the motion of the device if one or more flashes are not detected, for example due to a blockage of the detector 103.

According to some embodiments of the present invention, the operator detects when the plate 134 is permanently in a lower position. In that case, it may take a few treatment sessions for the operator to adapt to the autonomous repetition rate of care taking executions of device 102 as also depicted in the first two events in FIG. 7.

As described above, the dermatologic care tool 102 may be an IPL handpiece that incorporates a handle. The handle allows the user to maneuver the device 100 that is attached thereto, as described above. Such a dermatologic care tool 102 includes a treatment light source and a light guide that is in contact with the skin, for example as shown at FIG. 1. In each session, the dermatologic care tool 102 emits a pulse of light, such as infrared light, which penetrates the skin. For example, each emission has duration of between about ~100 microseconds and about ~200 milliseconds, for example ~15 milliseconds, and an energy density of between about ~5 and ~40 Joules/cm2, for example ~20 Joules/cm2 depending on the light source type. The pulse wavelength is between about 400 nm and about 1500 nm in the case of an IPL. When treating large areas, the IPL is operated in an automatic repetitive mode where a pulse is released every 1-4 seconds. Other repetition rate may range between 1-2 pulses per second, for example when the dermatologic care tool 102 is LightSheer™ device, and about one pulse every 3-4 seconds, for example when the dermatologic care tool 102 is Alma™ IPL or Lumenis™ Quantum device. The repetition rate may be 1-10 pulses/sec for a Q switch laser, and 0.5-2 pulses/sec for a CO2 laser used in skin resurfacing. For clarity, the device 100 may be set according to the movement or moving rate of the roller 105 and/or the illumination rate. As a non limiting example, while moving from one skin subarea of 1 cm length to another in a treatment repetition rate of 1 pulse/sec the device movement speed has to be higher than 1 cm/sec. The movement rate may be considered as 1 cm per second though the actual movement is faster as the waiting time for illumination to occur and the illumination takes time as well. There is a relation between both quantities, since operators adjust the manual force they exert on the treatment device to the pulse repetition rate.

Figure 8:
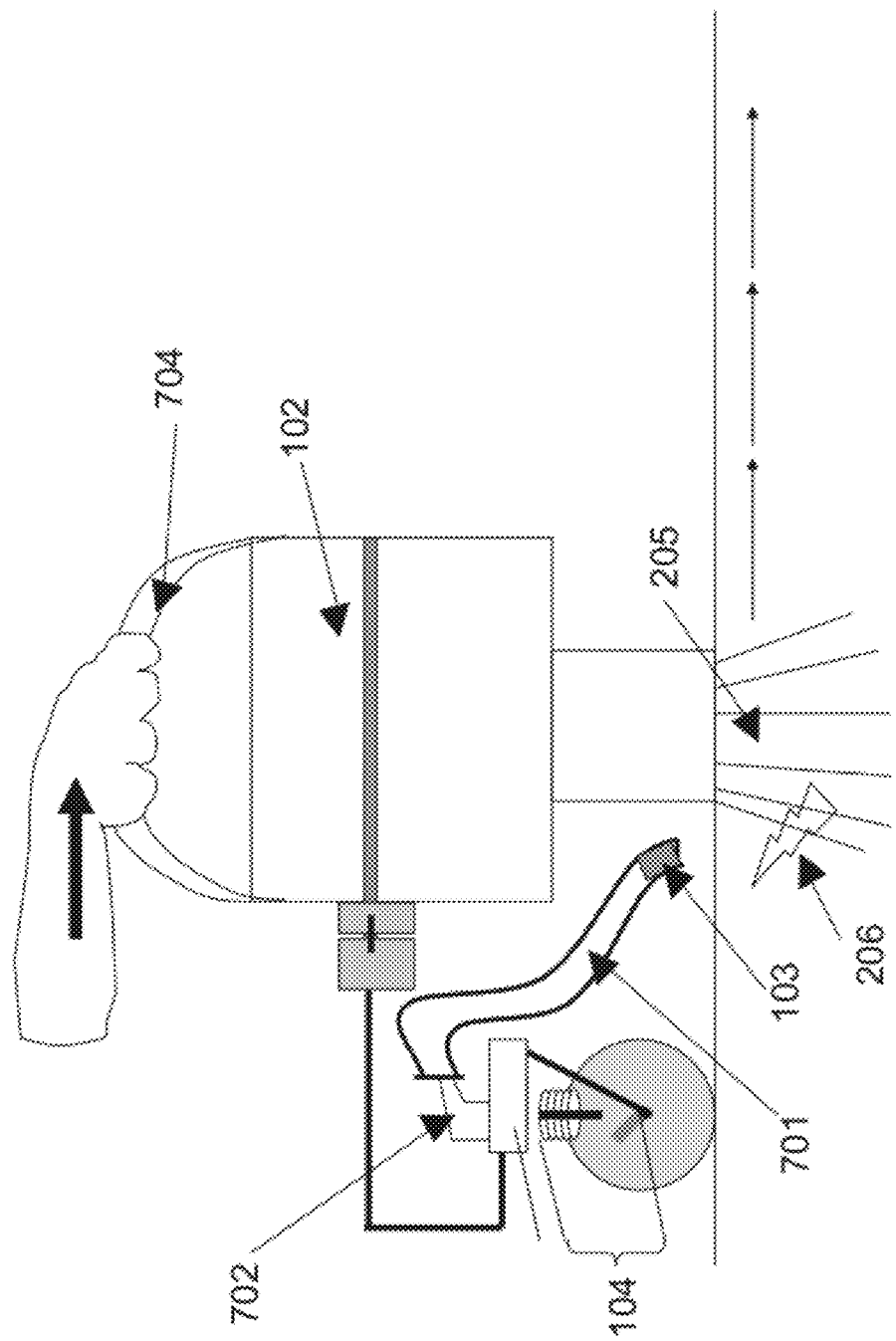
FIG. 8 is an exemplary device for guiding a multiple area dermatologic care process according to monitored emission of light beams, such as pulsed laser beams, according to some embodiments of the present invention.

Reference is now made to FIG. 8, which is an exemplary device 700 for guiding a multiple area dermatologic care process according to monitored emission of light beams, such as pulsed laser beams, according to some embodiments of the present invention. The device includes a support 701 that directs the face of the detector 103 toward the skin subarea so as to allow it to sense light 206 scattered from the skin when an IPL handpiece or laser dermatologic care tool 102 emits a treatment beam 205 onto a certain skin subarea. The support 701 is optionally an arm that holds the detector 103 in proximity to the skin sub area, for example few centimeters from the skin subarea. As the detector 103 is directed toward the skin subarea and placed in a short distance therefrom, it is more sensitive to reflections therefrom and less sensitive to ambient light signals from external illumination sources and flashes, even if they have a similar pulse duration and intensity. Optionally, the support 701 is made of a flexible stem. In such a manner, the location of the detector 103 may be adjusted according to the dermatologic care tool 102 used for performing the dermatologic care sessions. The support 701 is optionally connected to a mount 702 attached to the carrier device. Optionally, handle 704 attached to the dermatologic care tool 102.

In another embodiment of the present invention the device 100 includes a hand fixation element that fixes the operator's arm in relation to the device 100 during the multiple area process. For example, as shown at FIG. 9, the carrier 101 is physically connected to a strapping mechanism 141 that includes an elastic band that fixes the device 101 to the operator's arm. In such a manner, the device 100 may be stably driven along a straight strip of the large area of skin 99.

As described above, different dermatologic care tools with different sizes may be used and the location of the detector 103 may be adjusted accordingly. The signal from detector 103 is used for controlling the brake unit 104 as described above.

Figure 3B:
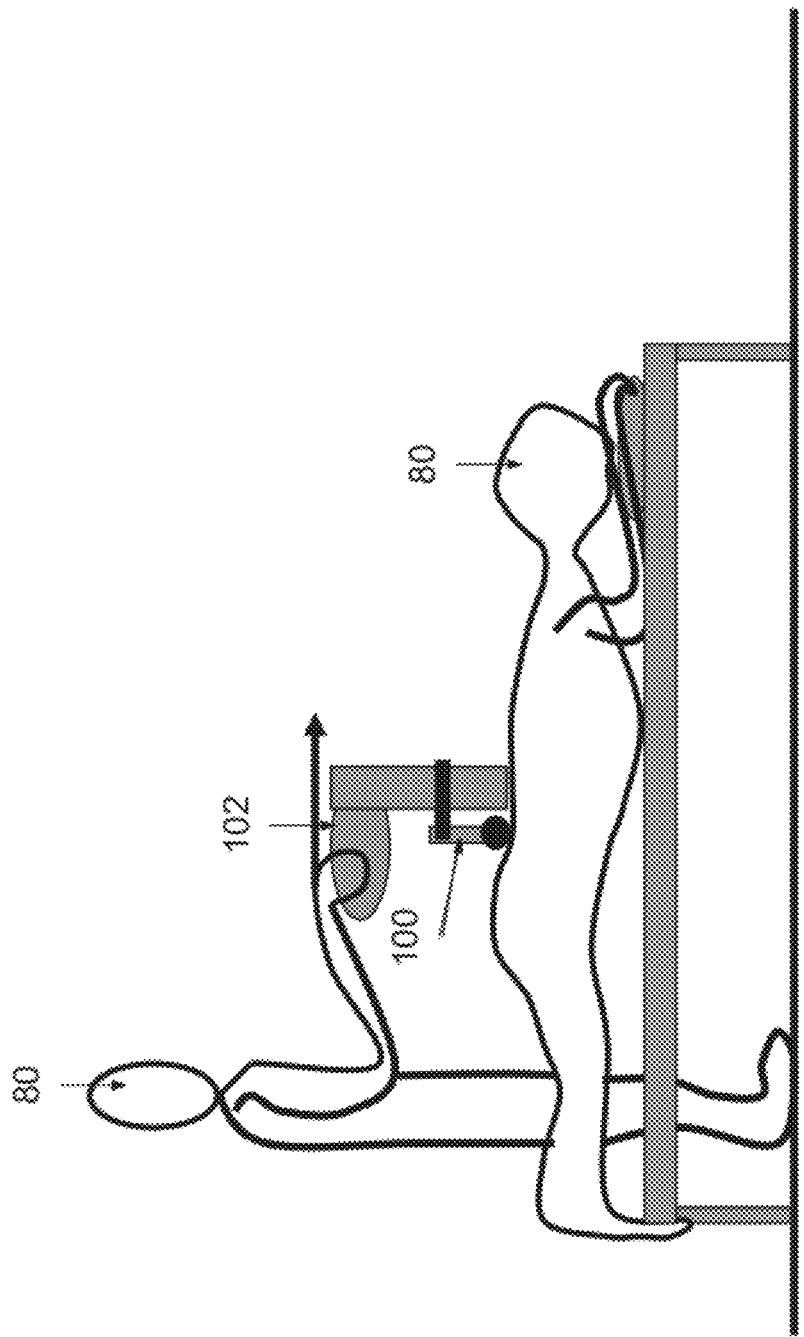
FIG. 3B is a schematic illustration of an operator that manually glides a dermatologic care tool using the device depicted FIG. 3A, according to some embodiments of the present invention.

Reference is now made, once again, to FIG. 3A which depicts an exemplary device that regulates the maneuvering of a dermatologic care tool 102 according to a movement tracker, according to some embodiments of the present invention. The carrier 101 and the supported dermatologic care tool 102 are as depicted in FIG. 2A. However, In FIG. 3A the brake unit 104 includes a movement halting mechanism that is located in a wheel 219 having a radius R. The movement tracker indicates a passage from one skin subarea to another so as to allow regulating the driving of the dermatologic care tool 102 without controlling its internal operation, for example without controlling or effecting the emission of light, the capturing of an image and the like. In FIG. 3A, the length of each skin subarea is denoted with L. While manually pushing the device 101, for example by hand 212, the wheel 219 rolls freely in one direction. For example, FIG. 3B depicts an exemplary operator 80 that glides the device 100 over the back of a patient 80. The operator 80 holds the dermatologic care tool 102, which is optionally a head of a hair removing system, during the gliding. The device 100 regulates the movement of the dermatologic care tool 102 over the large skin area on the back of the patient 80 according to the movement of the device 101 and/or the dermatologic care sessions, for example as described below and outlined above.

The exemplary movement tracker includes a frame 120 that supports the wheel 219 and has a frame extension, such as a plate 124. A rotating extension 123, such as a rotating plate 123, is attached to one of the sides of the wheel 219. The extensions 123, 124 are placed on a common plane, perpendicular to the rotation axis 220 of the wheel. In such a manner, the extensions 123, 124 collide once every full turn of the wheel 219. In such an embodiment, the radius of the wheel is set according to the distance between the centers of two neighboring skin subareas D. For example $R=D/2\pi$. In such a manner, the collision occurs when the wheel rotates a distance that is equal to D, namely when the devices moves from the center of one skin subarea to the center of a neighboring skin subarea. Optionally, the rotating plate 123 has a relatively high flexibility coefficient, denoted herein as B. The flexibility coefficient may be is set by the composition of at least one of the extensions 123, 124 and/or their thickness. In such an embodiment, the rotating extension 124 bends after collide with the frame extension 123. The bending is expressed in an increment to the impedance felt by the actuating operator. FIG. 10A shows an exemplary wheel 219 with a rotating extension having a bending angle $\theta$. FIG. 10B depicts an exemplary graph where $\theta$ denotes the bending angle and the notations of X-axis denote the distance from the center of the first skin subarea. This impedance applied by the bending may be a sign to the operator to slow down the device 101 and/or to stop the device 100 until she receive an indication that a dermatologic care session occurs, for example until she sees the illumination of a pulsed laser beam. Optionally, the flexibility coefficient is set as sufficient to slow down the movement of the device 100. The slowing down level depends on how fast the operator pushes the device 100. It should be noted that when some dermatologic care tool 102 are used, the operator may receive indication about the performance of a session without directly looking at the treatment site. The operator may see reflections of the pulsed laser beam from the walls of the treatment room. Each time the operator sees a pulse of light, she automatically reacts by pushing device 100 more vigorously to overcome the impendence applied by the brake unit 104. Optionally, the rate of sessions is approximately 1-2 pulses per second for laser based epilation tools and/or 1 pulse per 3 seconds for epilation tools, such as IPLs.

Figure 11B:
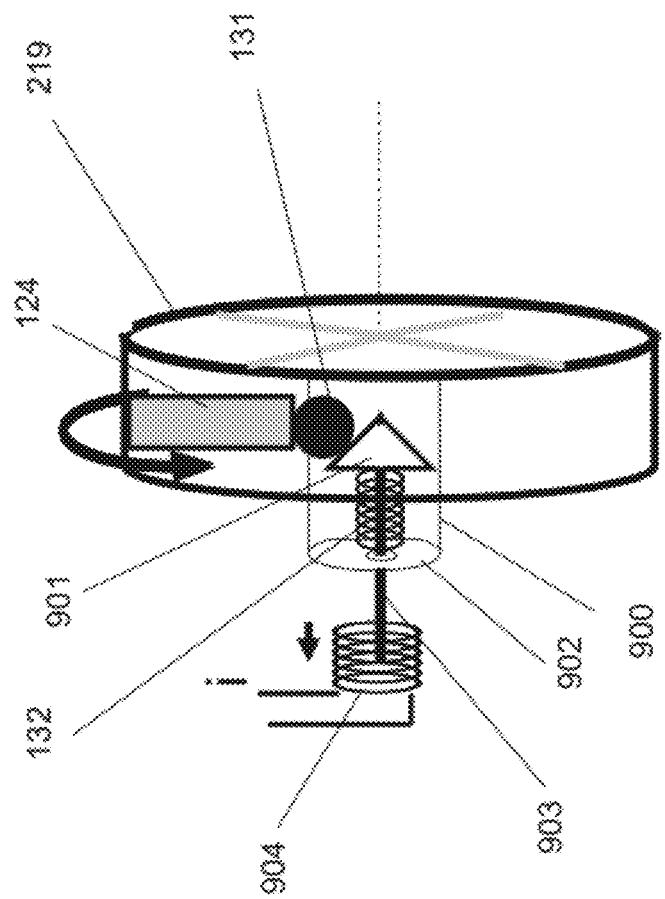
FIG. 11B is a schematic illustration of an exemplary wheel and an exemplary shaft of an exemplary brake unit, according to some embodiments of the present invention.
Figure 11A:
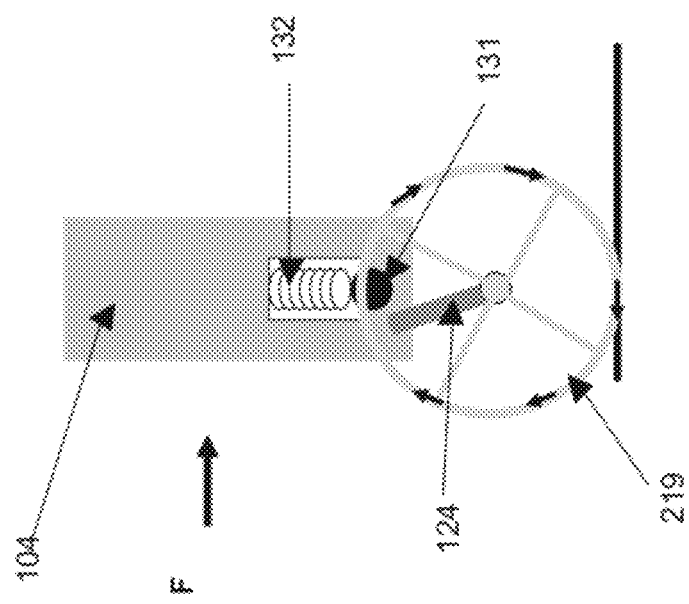
FIG. 11A is a schematic illustration of a brake unit in which a ball is used instead of a plate to regulate the movement of a dermatologic care tool, according to some embodiments of the present invention.

As shown at FIG. 11A, a ball 131, which is pressed by a spring 132, may be used instead of the frame plate 123, in some embodiments of the present invention. In such an embodiment, the impedance is determined according to the flexibility coefficient of the spring 132. One or more of the extensions may be selected to fit to the operator, for example according to a calibration process.

Optionally, the rotating plate 123 or spring 131 may be adjusted such that the operation of the braking mechanism fits a working plan practiced by the operator and/or her comfort. Different springs or plates may be provided in a kit supplied to a customer. As described above, the device 100 may be used for guiding a number of different dermatologic care tools for performing a multiple area dermatologic care process for examining, diagnosing and/or treating a large skin area. Each one of these dermatologic care tool may have a different rate of dermatologic care sessions, a different length of each dermatologic care session, and/or a different working area that is adjusted for skin subareas with different sizes. Optionally a kit that comprises a plurality of different braking mechanisms or parts thereof is provided. Each member of the kit, for example, a braking mechanism, a wheel, and/or a brake fits the characteristics of a different dermatologic care tool. For example, some wheels may have a larger radius and some may have smaller radius. When the radius is larger, the plate 124 meets the rotating extension 123 after it rolls a larger distance. When the radius is smaller, the plate 124 meets the rotating extension 123 after it rolls a smaller distance. In such a manner, the kit facilitating the adapting of the guidance to different dermatologic care tools with different working areas.

Reference is now made to FIG. 11B, which is a schematic illustration of a wheel 219 and a designated shaft 903 of a brake unit 104, according to some embodiments of the present invention. As depicted in FIG. 11B the plate 124 is located on the inner side of the rim of the wheel 219 and rotates with it. Ball 131 is located in a cylinder 900 which is rigidly connected to device 100. The ball partially bulges from a hole in the cylinder 900 when pushed as described below. A spring 132 is located inside the cylinder 900, around the shaft 903 and pushes a conical element that pushes the ball upward, resulting in partial bulging of the ball 131. When the plate 124 collides with the ball 131, it is halt unless a relatively strong force that is applied by the operator so as to overcome the spring compression. In another embodiment, the resistance of the ball 131 to the motion of the wheel 219 is released with the aid of a solenoid 904 that pulls the conical element leftward while a current is driven through it. Optionally, the releasing current is applied upon the detection of light signal 114, as described above and depicted in FIG. 7. An advantage of the embodiment depicted in FIG. 11B is the capability to seal the entire mechanism in order to prevent gel from entering the mechanism of the brake unit 104.

Optionally, a number of extensions are attached to the wheel 219. Similarly, the rotating extension 123 is placed so as to collide with the frame extension 124 twice each full rotation, for example as shown at FIG. 12. When N rotating elements are attached to the wheel 219, a larger wheel, with radius R, may be used for achieving identical advance steps, each of a distance $L=2\pi R/N$. It should be noted that a using a relativity large wheel, for example having a radius of about 7-20 mm, enhances the accuracy the regulation. Some multiple area processes, such as epilation processes, involve covering the large skin area with a layer gel, such as topical anesthetic gel and/or a cooling gel, such as a conductive gel laser hair remover of Ab Sonic Gymnic TENS U. Such a layer of gel may reduce the accuracy of the guidance provided by the device as it may cover the wheel. However, if the radius of the wheel is large, the layer of gel cannot cover the wheel and therefore has less effect on the accuracy of the guidance. In addition, the wheel axis will not be covered by gel, which dries and gets sticky and/or slippery. As an example, an advance of L=1 cm, which may be the length of a skin subarea when the dermatologic care tool 102 is an hair removal system, such as a head of a LightSheer™ system of Lumenis™ that the specification thereof is incorporated herein by reference, may be easily achieved with a wheel having a 1.05 cm diameter and equipped with 3 rotating elements having an angle of 120° between each couple of them rather than a wheel with a diameter of about 3 mm that may be easily covered with gel.

Optionally, the diameter of the wheel 219 is adjusted to the properties of the dermatologic care tool 102. Optionally, the property is a friction coefficient between an oily or a wet skin surface and the face of the dermatologic care tool 102 that is placed thereon, for example a light guide of an IPL based device. Optionally, the property is the weight of the dermatologic care tool 102 or the lead thereof and/or the thrust of user that pushes the device.

Figure 13:
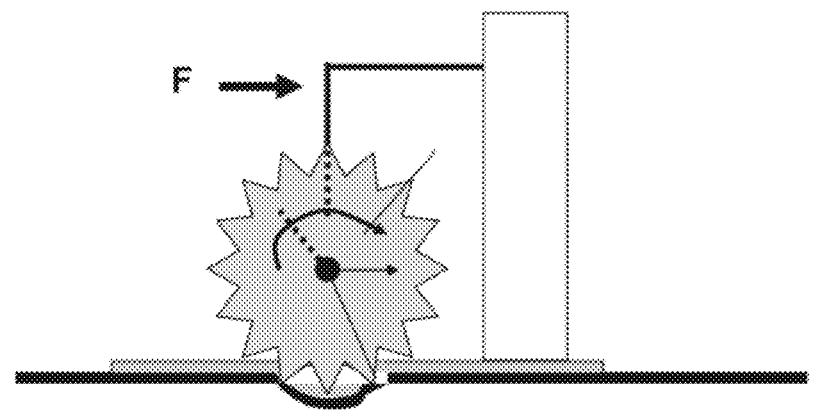
FIG. 13 is a schematic illustration of a brake unit having a toothed wheel for regulating the movement of a dermatologic care tool on wet or otherwise slippery skin, according to some embodiments of the present invention.
Figure 14:
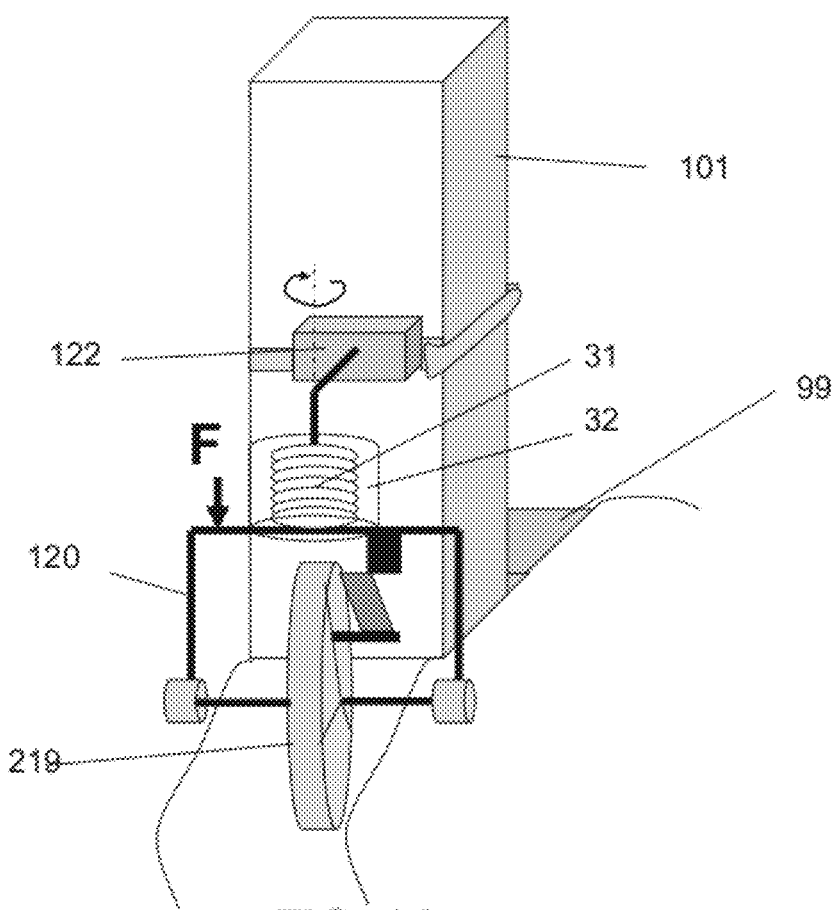
FIG. 14 depicts a brake unit, according to some embodiments of the present invention.

Optionally, the wheel 219 is toothed, for example as a cogwheel, for example as shown at FIG. 13. In such an embodiment, the peripheral teeth 312 increase the friction with the skin and reduce the slidability of the device 102 on a skin area layered with gel. Non limiting examples of methods of producing a toothed wheel according to the current invention are mechanically shaping the wheel periphery surface by coating and the wheel base with a layer or a rough surface with a texture of a sand paper. There is a tradeoff between friction and patient comfort when is come to the thickness of the applied layer of gel and/or the length and/or sharpness of the cogs/teeth of the wheel. For example, sharp teeth may be uncomfort however if sharpness is compromised, the wheel may slide when gel is used. Optionally, a wheel with an outer periphery coated with a powder of Aluminum Oxide crystals is used. Such a powder is found on sanding paper "superflex closed back abrasive" fine grade 120, produced by Saint Gobain abrasive Ltd., UK, which the specification thereof is incorporated herein by reference. The sharp edges found in micro-crystal fragments, in contrast to smoother edges of non crystal fragments such as glass, provides high friction. The small size of the micro-crystal fragments, approximately 125 micron, provides relative skin comfort in spite of their highly sharp edges. According to some embodiments of the present invention, the brake unit 104 may be adapted to regulate the movement of the carrier 101 in non planar surfaces. For example, FIG. 14 depicts a brake unit, as depicted in FIG. 7 however further includes a spring 31 for maintaining contact between the wheel 219 and the skin 99 when the movement trajectory of the dermatologic care tool 102 and the surface of the skin 99 are not parallel. The spring 31 pushes the wheel 219 and the frame 120 toward the skin 99. In such a manner, the impendence applied on the rotation of the wheel 219 affects the movement of the carrier 101 even in curved surfaces, such as the skin surfaces of the limbs.

Figure 15:
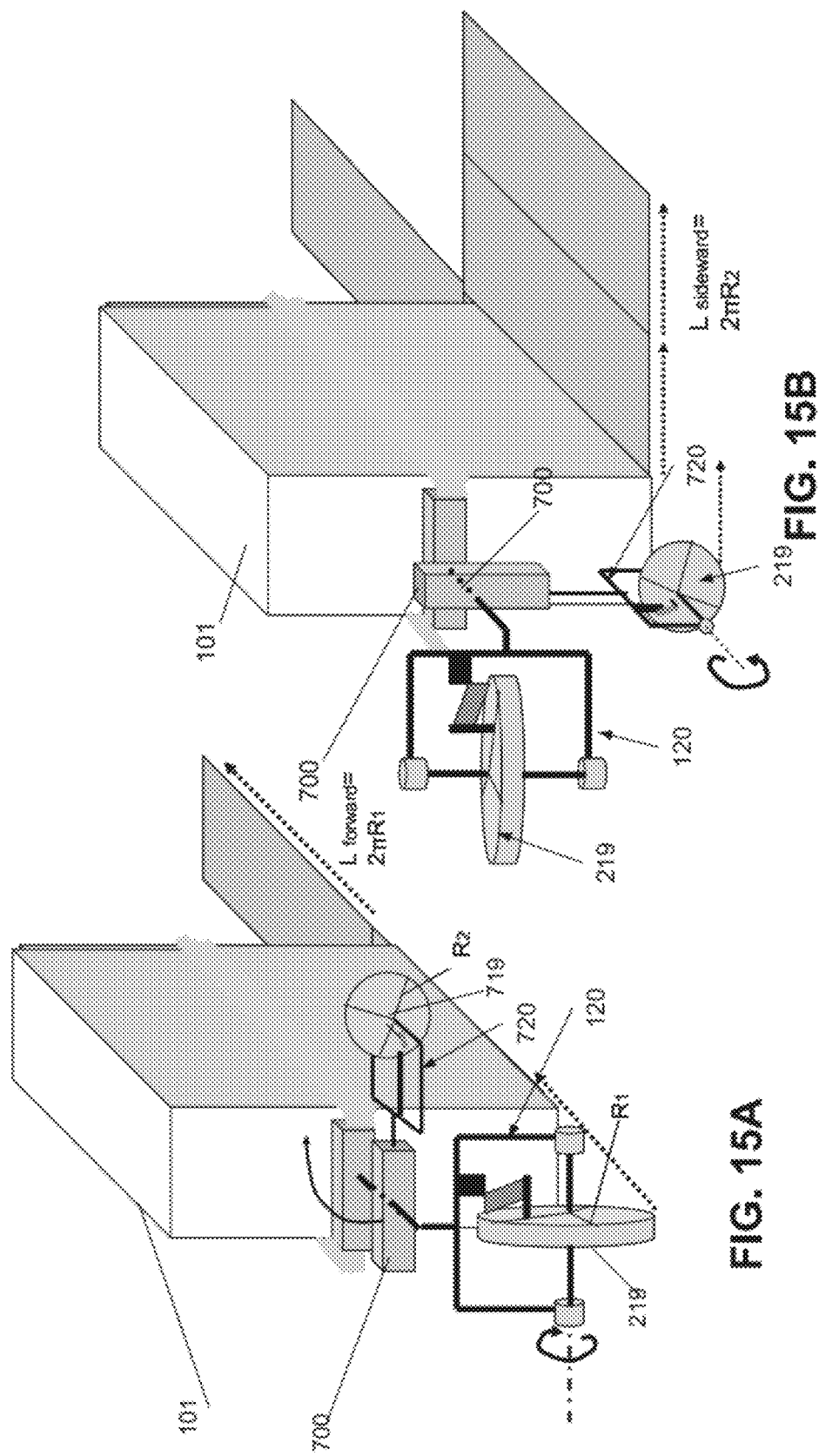
FIGS. 15A and 15B are schematic illustrations of a device adapted regulate the movement of the source in two dimensions, according to some embodiments of the present invention.

According to some embodiments of the present invention, the brake unit 104 may be adapted regulate the movement of the dermatologic care tool 102 in two dimensions. In such an embodiment, dermatologic care tool 102 may be maneuvered during a single multiple area process, from one side of the large area of skin to another side of the large area of skin, and from the top of the large area of skin to the bottom of the large area of skin. For example, reference is now made to FIGS. 15A and 15B which are schematic illustrations of a device, as depicted in FIG. 3A, where the brake unit 104 includes two frames 120, 720 that support two different wheels 219, 719 having orthogonal rotation axes. The frames 120, 720 are orthogonally connected to a common rotational element 700 that can be maneuvered to allow one of the wheels 219, 719 to be in separately contact with the skin 99 while the other wheel 719, 219 is free. In use, the optionally rotates the common rotational element 700 to establish contact with one of the wheels 719, 219 according to the direction in which the device is maneuvered.

In such an embodiment, the radius of each one of the wheels 219, 719 is adapted to the respective dimension of the skin subarea that is examined, treated, and/or diagnosed by the dermatologic care tool 102. For example, in FIGS. 15A and 15B the radius of wheel 219 is adapted to distance between the center of one skin subarea and the center of a proximate skin subarea which is located when moving the carrier 101 forward and the radius of wheel 719 is adapted to distance between the center of one skin subarea and the center of a proximate skin subarea which is located when moving the carrier 101 in an orthogonal direction, sideward. As an example, if the dermatologic care tool 102 is an IPL treatment head having the size 40 mm×10 mm, there is a need to push the IPL head 40 mm forward or backward and 10 mm sideward. The advance of device 100 by a length L=3 cm, requires a wheel of diameter $3/\pi<1$ cm. As a result, the entire intermittent driving assembly can be as small as approximately 2-3 cm.

Figure 16:
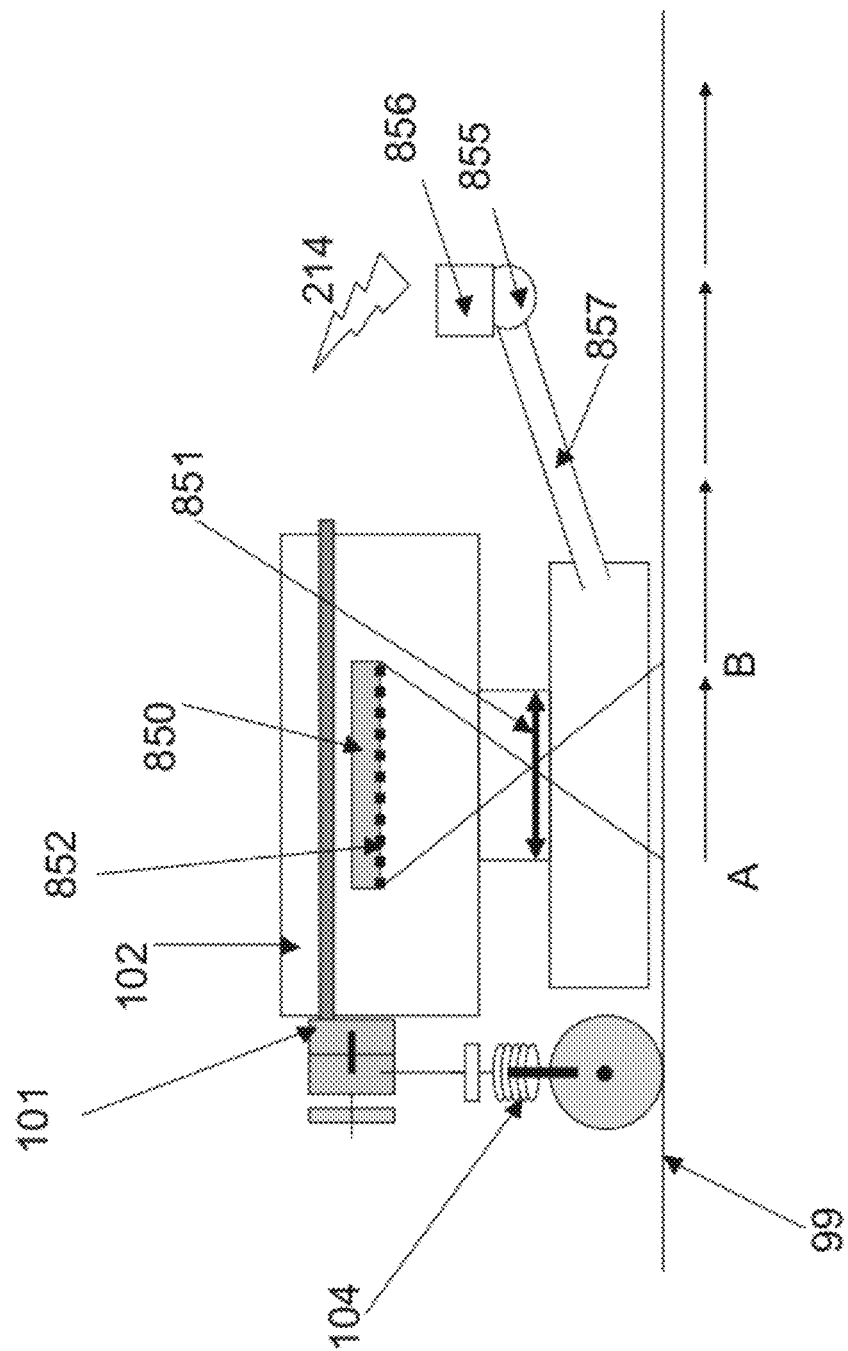
FIG. 16 is a schematic illustration of a device for diagnosing pigmented lesions, according to some embodiments of the present invention.

Reference is now made to FIG. 16, which is a schematic illustration of a device 800 for diagnosing pigmented lesions, according to some embodiments of the present invention. The carrier 101 and the brake unit 104 are as described above; however FIG. 16 depicts a dermatologic care tool 102 that supports an imaging device for imaging a large skin area for diagnosis.

Such a device 800 may be designed for the detection of lesions with cancerous patterns and/or lesions in a pathological condition by an untrained person. Optionally, the dermatologic care tool 102 is a camera, such as a commercial digital camera, which is manually pushed by the operator. The camera has a sensor 850, such as a CCD based sensor and a lens 852. Optionally, a light guide 851, such as a block of glass and/or plastic, is placed in front of the camera 102. Optionally, the light guide 851 is transparent and polished on side that faces the skin 99 and in the side which is oppose thereto and optionally painted with diffusing white color covered by black color on the sides. Optionally, the light guide 851 includes an extension 857, such an optic fiber, which may be integrated into the light guide 851. A light source 855, such as an element of one or more flash lamps, is connected to the extension 857 and directed to emit white light towards the extension 857. In such a manner, the light guide 851 provides homogeneous illumination to area AB when the light source 855 flashes. The camera 102 is optionally a video camera, or a camera in a video mode, with an autofocus mechanism that continuously capture images of the skin 99. The brake unit 104 is optionally activated by a light detector, for example as described above. In such a manner, the movement of the device 800 is regulated according to the flashes of the light source 855. In use, the light source 855 is repetitively activated, for example every 0.5 second where the flashes time the brake unit 104. The operator pushes the device 800 on the skin surface 99 where the advance is regulated by the brake unit 104, for example as described above. When the brake is released, the device 800 may be easily advanced since there is no resistance. After the device 800 is pushed a distance, for example the distance AB=L=$2\pi R$, where R denotes the radius of the wheel of the brake unit 104, the brake is activated and the resistance increases. In such a manner, the device 800 is substantially stationary when the light source 855 is triggered and a high quality picture may be obtained. Such a repetitive process allows sequentially imaging proximate skin subareas of a large skin area without, or substantially without, misses or overlaps. The camera may operate independently of the device 800 and not triggered by it or by any other unit or device. In such an embodiment, the device 800 may be used for guiding almost any commercial camera.

Optionally, the device comprises an analysis unit for processing the video captured by the dermatologic care tool 102. The analysis unit may identify the frames that clearly depict the skin subareas, for example according to their brightness. The analysis unit may be part of the dermatologic care tool 102 and/or external thereto, for example firmly or detachably attached to the carrier 101.

The camera may also be operated is a repeat mode which sequentially captures images. If the flash of the camera is turned on, by promptly pushing the carrier to its halting position and waiting until the camera takes a picture, the camera flash releases the brake as previously described and a series of high quality pictures are obtained.

Optionally, a calibration image of the starting point is taken before the device 800 is driven over the skin of the patient. The calibration image allows repeating the aforementioned imaging process in a substantially similar manner. In such a manner, a frame by frame comparison may be made as the order in which frames are taken is identical. Optionally, the calibration image is taken by marking a certain mark 221 on the skin of the patient. Optionally, the mark indicates in which trajectory the device 800 should be driven.

Optionally, the video captured by the dermatologic care tool 102 and/or frames thereof are transmitted to a remote terminal, for example via the internet, for analysis. Optionally, the data is transmitted using a wireless interface, such as a cellular interface and/or a Wi-Fi interface which is placed in the device 800. Optionally, an electronic circuit tags the frame numbers to assist in finding differences in the remote terminal which receives the transmitted data. In such an embodiment, the device 800 is used as a telemedicine device for early skin cancer detection by the guidance which is described herein.

FIGS. 17A and 17B depict exemplary skin area 299, human torso, and a set of proximate skin subareas 299 which are sequentially imaged by the device depicted in FIG. 16 in two different periods, according to some embodiments of the present invention. The areas 224 between the subareas, which are pictured in respective frames, are dark and/or blurred as they where not illuminated and/or as the device 800 has been moved during the capturing thereof. Each image in the set is of a sequential equidistant skin subarea. In FIG. 17B the same skin area 299 is imaged after a certain period, for example one month, one year and/or any intermediate period.

It should be noted that as the intermittent movement of the device 800 in synchronized according to the flashes of the light source 855, captured frames may be matched with other captured frames in the order of their taking. Frame #n depicts the same skin subarea in all the videos captured as described above, as long as the starting point and movement trajectory are the same and the light source 855 flashes according to the same tempo. As a result any change of pigmentation and/or the number of lesions 222, 223, for example the number of moles, may be detected be a match, optionally without any image alignment and/or registration. As an example, if frame number 89 in the first captured video shows a mole, the same mole is depicted in a respective frame in the second captured video. Such image capturing allows simultaneously displaying respective frames of a certain lesion to a user, such as a physician and/or forwarding the respective frames to an analysis unit. If pigmentary change is depicted in a certain frame of a video captured in a second imaging session, it is easily detected when matched a respective frame which has been captured before the pigmentary change occurred. In such a manner the time that it takes to diagnose and detect changes to moles in large skin areas is reduced, for example to 10 seconds per frame or less. If, for example, the skin area is a back area of approximately 40 cm×50 cm and each frame has a size of 2 cm×2 cm, 20×25=500 frames have to be taken. By sequentially advancing the device 800 the back area may be photographed and optionally analyzed, within 250 seconds, namely in less than 4.5 minutes.

Reference is now made to FIG. 18 which is a schematic illustration of an exemplary universal strapping mechanism that enables the strapping of dermatologic care tools 102 in a large variety of sizes and shapes, according to some embodiments of the present invention. The strapping mechanism enables the strapping of an intermittent advance device 17, which is optionally defined as device 100 in FIG. 1, to various dermatologic care tools 102 such as IPL tools. The strapping mechanism comprises of a bracelet 187 having segments 188 which are connected by an axis 1812 that provides flexibility in one direction. Optionally, the bracelet 187 is similar to currently available watch bracelets. However, a soft layer 189 is added to the segments 188, for example a layer 189 of silicon based layer having a thickness between about 1 mm and about 5 mm. The soft layer 189 conforms the bracelet 187 to the slope and/or shape 182 of the dermatologic care tool 102 which is used, for example to an IPL having a truncated cone shape. The soft layer 189 also increases the friction between the bracelet 187 and the housing of the dermatologic care tool 102. A stretching element 1810 enables tightening of the bracelet 187 until the layer 189 is compressed. Optionally, a series of bracelets (not shown) is used in order to conform to a dermatologic care tools with a large size, for example having a diameter of 10-150 mm.

One or more of the segments 188 is rigidly connected to a plate 186 that is rigidly connected to a spherical joint 184 having a metallic sphere 183. The metallic sphere 183 is rigidly connected to the device 17. It is thus possible to drive the device 17 in any direction 1811, for example similarly to the described above. This enables the attachment of the bracelet 187 to both horizontal and/or vertical sections of the dermatologic care tool 102. A tightening screw 185 provides stability to the device 17.

As described above, the dermatologic care tool 102 may be a treatment device, such as a light based device, for example an IPL unit, an acoustic treatment device, and or a tactile treatment device, such as a device that generates tactile stimulations and/or emits buzz tones. As the movement of the device 800 is regulated according to the operation of the treatment device, the operator can maneuver the device with less effort and/or attention. As the device 800 does not require external triggering of the dermatologic care tool 102, the device 800 may be adapted to almost any dermatologic care tool 102. Treatment devices, which are based on light, include skin lesions treatment, hair removal treatment, skin tightening treatment, acne treatment, Tattoo or pigmentation removal treatment, skin resurfacing with and without Fraxel, IPLs or laser based devices, such as produced by Lumenis™, Syneron™, Alma™, Palomar™ Candela™, Quantel™ and the like. Care devices which emit monopolar or bipolar skin treatment energy and may be used in conjunction with device 800 are produced by Lumenis™, Syneron™, Alma™, Thermage™ and the like. As described above, the device may be firmly fixed to a treatment, diagnostic, and/or examination tool and/or used for guiding various independent tools. Such a device may be used as add-on to existing dermatologic care tools 102 for reducing the effort and/or attention required for performing sessions and/or to increase the accuracy of these performing sessions.

Reference is now made to FIG. 19, which is schematic illustration of a device with a mechanism for replacing detachable intermittent advance rollers in a large variety of sizes and shapes which are adapted to guide different dermatologic care tools, on slippery wet skin as well as on dry skin, according to some embodiments of the present invention. The device 1900 is set to support a detachable wheel 1901 made from rubber which provided adequate friction against forward or backward pushing force direction F. A solenoid is in the rectangular box 1902 while the braking mechanism is in the bottom of a rectangular box, as indicated by 1903. The braking mechanism utilizes a spherical ball which is bulged from a shaft 1904 of the wheel 1901 and collided with a rod that is compressed downward by a spring located in the solenoid in an OFF state when current is not flowing through the solenoid. The spring constant was selected to be high enough to ensure stopping the roller when the ball collided with the rod, even when the roller and the treatment device are pushed by the operator. On the other hand, the spring constant is weak enough to enable the operator to overcome the stopping mechanism when willing to do so, such as in case of malfunction of a brake release control circuit. The time duration between the activation of the solenoid by an electrical current, which releases the brake, and its deactivation, by stopping the current, which receives a ready to stop the wheel indication when the wheel completes a round, has been selected to be 180 millisecond. This time duration is long enough to enable the pushing hand to react to the sensation of reduced impedance and move the roller and short enough to ensure stopping the roller on the right treatment position on the skin when hand operator moves the roller at a high speed. The capability to set this time duration according to the laser or IPL flashing rate, as well as the individual operator reaction time, is advantageous. As a non limiting example, the time duration may be in the range of approximately between 30 millisecond and 400 millisecond. The upper limit of 400 millisecond may be set in the case of slow IPLs which fire treatment pulses every 3 seconds and the operator wants to deliberately operate slowly, for example due to lack of experience. FIG. 19 depicts an adapter 1905 that enables strapping of the roller 1900 to a distal part 1906 of a commercial hair removal laser. The solenoid as well as its control circuit is optionally operated by an 18V DC current supply.

In another embodiment of the invention, a circuit is set to detect the pulse of treatment light emitted by the treating device and to deactivate the solenoid in response. The circuit has a counter which enables the counting of the number of pulses emitted by the treatment device during the entire treatment. This number is of interest to the treatment device operator and assists him/her in charging the fees from the patient.

This may be displayed on a designated man machine interface (MMI), such as a display. As described above, replacing one detachable wheel with another allows adjusting the dermatologic care sessions to the used different dermatologic care tool. This adjustment facilitate using different dermatologic care tools with different illumination rates and working areas, as described above.

It is expected that during the life of a patent maturing from this application many relevant systems and methods will be developed and the scope of the term dermatologic care tool, sensor, treatment device, diagnose device, and examination device is intended to include all such new technologies a priori.

As used herein the term "about" refers to ±20%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device of guiding a dermatologic care process in multiple skin areas, comprising:
    a carrier adapted to support a drive of a dermatologic care tool over a skin area while said dermatologic care tool intermittently performs a plurality of dermatologic care sessions each in one of a plurality of skin subareas of said skin area by emitting at least one pulse of treatment light for performing said dermatologic care session;
    a treatment light detector which generates a signal indicative of detection of at least one of a start and an end of each said dermatologic care session by detecting said at least one pulse of treatment light having energy for performing said dermatologic care session; and
    a brake unit configured to operate according to said signal from said treatment light detector, said break unit configured to regulate a movement of said carrier in response to said signal to guide said dermatologic care tool from being placed to perform a first of said plurality of dermatologic care sessions to a first of said plurality of skin subareas to being placed to perform a second of said plurality of dermatologic care sessions to a second of said plurality of skin subareas during said drive;
    wherein said dermatologic care tool and said light detector are electronically disconnected during said dermatologic care session such that said treatment light operates independently from said device.

2. The device of claim 1, wherein said dermatologic care tool is selected from a group consisting of: a handheld episcope, an electromagnetic energy (EM) transmitter, a conduit of such EM pulses, an intense pulsed light (IPL) epilator, and a laser tool.

3. The device of claim 1, wherein said carrier is sized and shaped to for detachably and alternately supporting a plurality of different dermatologic care tools.

4. The device of claim 1, wherein said brake unit comprises:
    at least one wheel operatively connected to said carrier and adapted to rotate during said movement, and
    at least one wheel brake which restrains a rotation freedom of said at least one wheel during said movement.

5. The device of claim 4, wherein said at least one wheel is at least partly covered with anti sliding material over gel.

6. The device of claim 4, wherein said at least one wheel is detachable.

7. The device of claim 4, wherein said at least one wheel is detachable and selected from a plurality of detachable wheels, each said detachable wheel being adapted to change said movement and said regulation in a manner which is adapted to at least one different dermatologic care sessions rate and different dermatologic care session skin subarea size of one of a plurality of different dermatologic care tools.

8. The device of claim 4, wherein said at least one wheel brake is detachable and selected from a plurality of detachable wheel brakes, each said detachable wheel brake being adapted to change said movement and said regulation in a manner that is adapted to at least one different dermatologic care sessions rate and different dermatologic care session skin subarea size of one of a plurality of different dermatologic care tools.

9. The device of claim 1, further comprising a learning module for learning a pattern of said plurality of dermatologic care sessions, said brake unit perform said regulating according to said pattern.

10. The device of claim 1, further comprising a light detector that detects said flashing, said brake unit regulates said movement according to said detection.

11. The device of claim 10, wherein said light detector is more sensitive to reflections of said flashing than to ambient light from an external illumination source.

12. The device of claim 1, wherein said movement is performed in two dimensions.

13. The device of claim 1, further comprising a strapping mechanism for clasping said dermatologic care tool to said carrier.

14. The device of claim 1, further comprising a counter for counting said at least one pulse of light.

15. The device of claim 1, wherein said carrier comprises an adapter which is adapted for supporting said dermatologic care tool, said adapter being detachable.

16. The device of claim 1, wherein said carrier is robotic and automatically driven.

17. The device of claim 1, wherein said brake unit comprises: at least one wheel operatively connected to said carrier and adapted to rotate during said movement; wherein said brake unit restrains a rotation freedom of said at least one wheel during said movement; wherein said at least one wheel is at least partly covered with a member of a group consisting of Aluminum Oxide crystals fragments, teeth, glass fragments, carburundum fragments, and at least one rubber layer.

18. A method of guiding a dermatologic care process, comprising:
mounting a dermatologic care tool in a carrier having a brake unit and an electromagnetic (EM) detector;
using said carrier for supporting a drive of said dermatologic care tool over a skin area while intermittently performing a plurality of dermatologic care sessions by emitting an EM treatment pulse in each one of a plurality of skin subareas of said skin area, said EM treatment pulse performing said dermatologic care session;
detecting, using said EM detector, which generates a signal indicative of at least one of the start and end of each said dermatologic care session during said drive according to said EM treatment pulse having energy for performing said dermatologic care session; and
operating said brake unit, in response to said signal, to regulate automatically a movement of said carrier over said skin area, from one of said plurality of skin subareas to another;
wherein said brake unit and said EM detector are electronically disconnected from said dermatologic care tool during said dermatologic care session such that said EM treatment pulse operates independently from said brake unit and said EM detector.

19. The method of claim 18, further comprising capturing an image of one of said plurality of skin subareas in each said care session.

20. The method of claim 18, wherein said regulating is performed according to distance traveled by said carrier during said movement.

21. The method of claim 18, further comprising learning a rate of said plurality of dermatologic care sessions and operating said brake unit according to said rate.

22. A method of guiding a dermatologic care process, comprising:
supporting a drive of a dermatologic care tool over a skin area of a patient;
automatically detecting a plurality of electromagnetic treatment pulses intermittently emitted by said dermatologic care tool by at least one light detector, said plurality of electromagnetic treatment pulses having energy for performing a dermatologic care session; and
operating a brake unit according to said plurality of electromagnetic treatment pulses to regulate said drive;
wherein said brake unit and said at least one light detector are electronically disconnected from said dermatologic care tool during said dermatologic care session such that said electromagnetic treatment pulses operate independently from said drive.

23. The method of claim 22, further comprising capturing a plurality of images of a plurality of subareas of said skin area during said drive and outputting said plurality of images for diagnosis.

* * * * *